United States Patent
Buss et al.

[19]

[11] Patent Number: 6,037,724
[45] Date of Patent: Mar. 14, 2000

[54] ELECTRONIC CONTROLLED SURGICAL POWER TOOL

[75] Inventors: Brian A. Buss; Rick A. Buss, both of Dallas, Tex.

[73] Assignee: Osteomed Corporation, Addison, Tex.

[21] Appl. No.: 09/069,349

[22] Filed: Apr. 29, 1998

Related U.S. Application Data

[60] Provisional application No. 60/045,246, May 1, 1997, provisional application No. 60/045,249, May 1, 1997, and provisional application No. 60/045,250, May 1, 1997.

[51] Int. Cl.⁷ .......................... H02K 51/00; A61F 17/23; H02P 5/50
[52] U.S. Cl. .......................... 318/71; 310/47; 310/68 A; 439/71; 606/180; 606/167
[58] Field of Search .................. 310/47, 68 A; 606/42, 177, 180, 170, 167; 173/217; 388/937; 439/38, 488; 336/90, DIG. 2; 364/474.21, 413.28; 433/99; 318/71; 601/87, 93, 101, 103

[56] References Cited

U.S. PATENT DOCUMENTS

| | | | |
|---|---|---|---|
| 3,463,990 | 8/1969 | Ross | 318/335 |
| 4,463,759 | 8/1984 | Garito et al. | 128/303.14 |
| 4,705,038 | 11/1987 | Sjostrom et al. | 128/305 |
| 5,093,593 | 3/1992 | Phillipp | 310/71 |
| 5,217,478 | 6/1993 | Rexroth | 606/180 |
| 5,247,128 | 9/1993 | Sven | 310/81 |
| 5,268,622 | 12/1993 | Phillipp | 318/254 |
| 5,269,794 | 12/1993 | Rexroth | 606/180 |
| 5,712,543 | 1/1998 | Sjostrom et al. | 318/71 |

*Primary Examiner*—Thomas M. Dougherty
*Assistant Examiner*—Burton S. Mullins
*Attorney, Agent, or Firm*—John E. Wagner

[57] ABSTRACT

A surgical power tool is disclosed including a power console and a handheld motor unit. The power console provides controlled power and to the handheld motor unit. Pressure sensitive switching elements on the handheld unit provide signals to the power console which are transformed into operating power to the motor unit including variable speed, speed range, forward/reverse, and safety. The handheld motor unit includes a chuck or tool receptacle and a Hall effect or other radiation field detector which response to the presence of a magnet or other radiation device as a part of the surgical tool, to identify the tool installed and provide a control signal to the motor, e.g., speed range limitation. The handheld motor unit housing is sealed and autoclavable. The housing for the handheld unit includes a flexible wall section lying over pressure sensitive switches and variable resistance whereby the surgeon's finger pressure on discrete portions of the flexible wall will provide motor control including speed control, direction of operation, speed range selection and a SAFE, i.e., locked off position. Multiple handheld motor units may be simultaneously operated and controlled individually by their handheld controls or selectively by the power supply and control unit. Footswitch control is also disclosed.

40 Claims, 40 Drawing Sheets

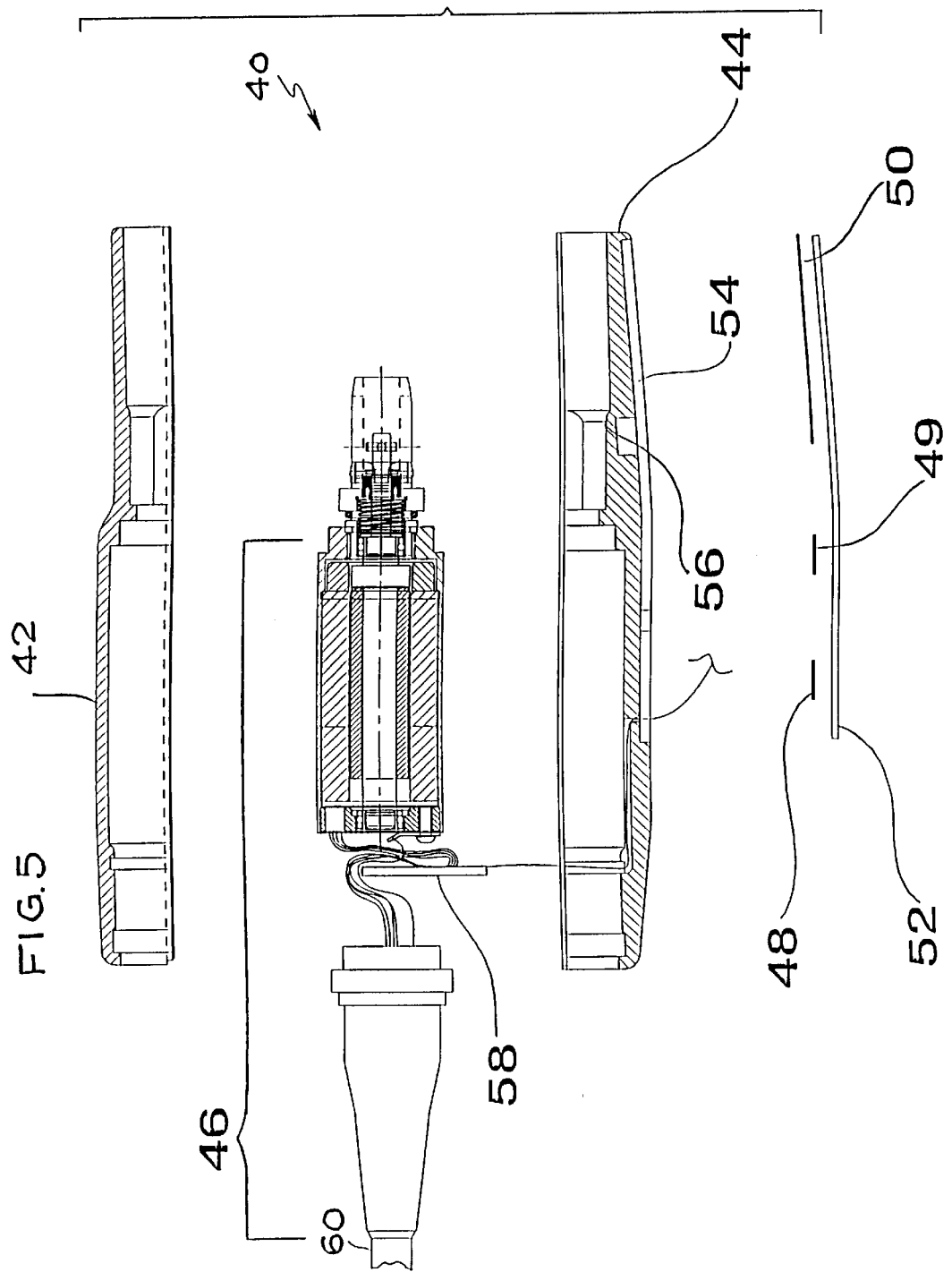

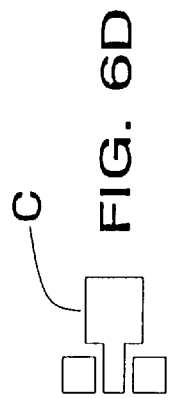
FIG. 6D
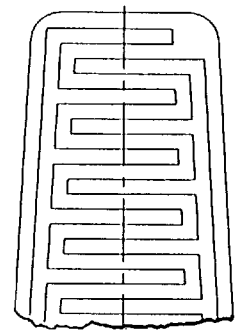
FIG. 6E
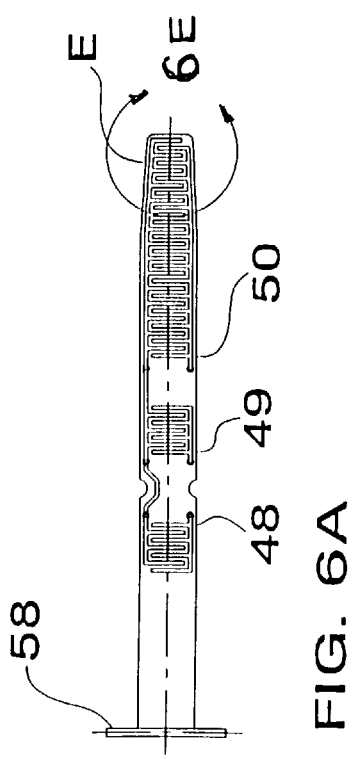
FIG. 6A
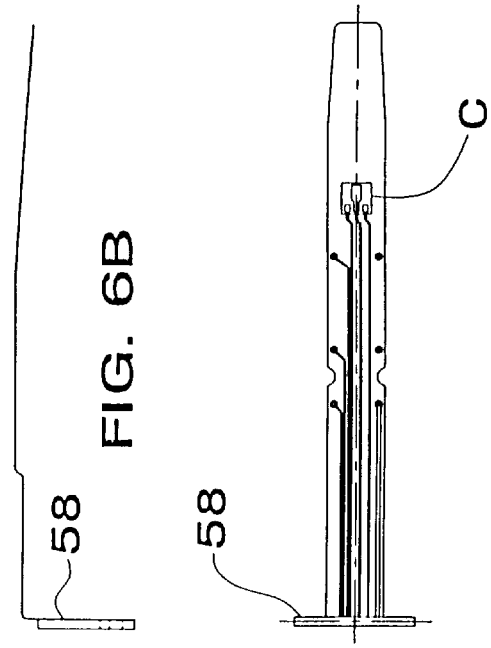
FIG. 6B
FIG. 6C

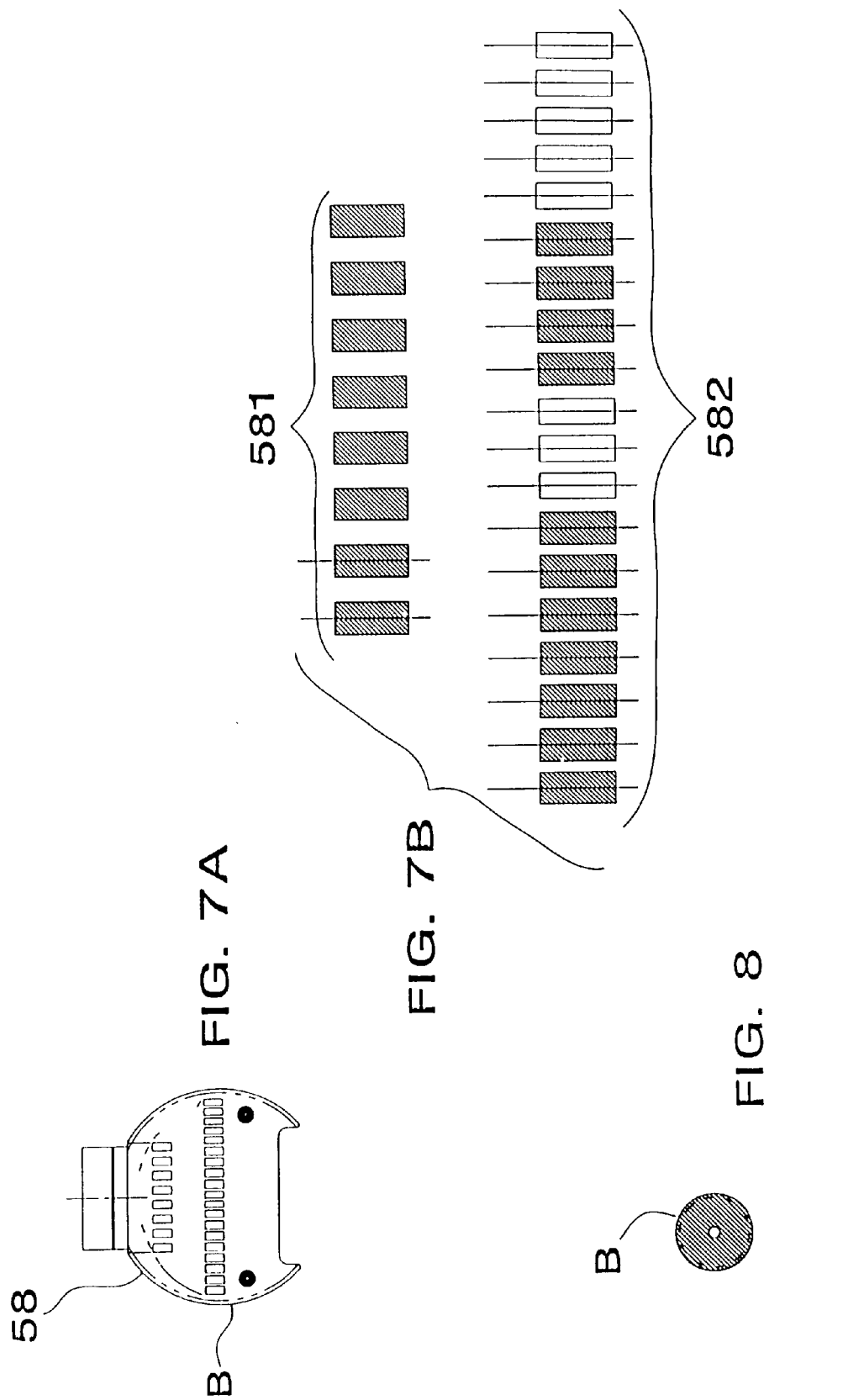

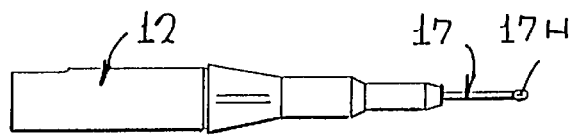
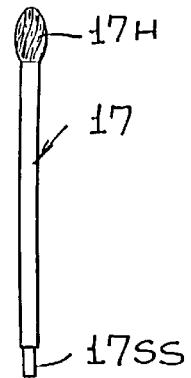
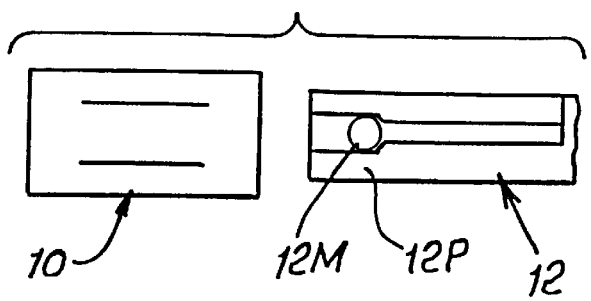
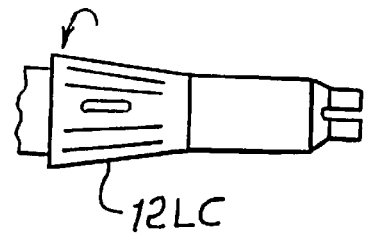
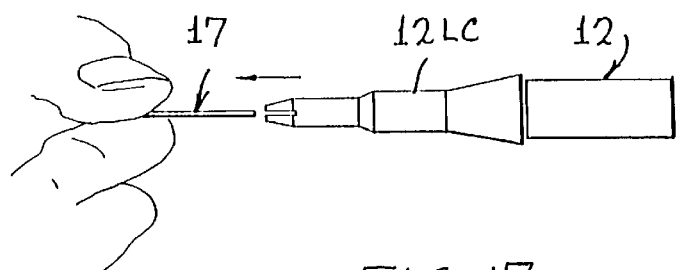
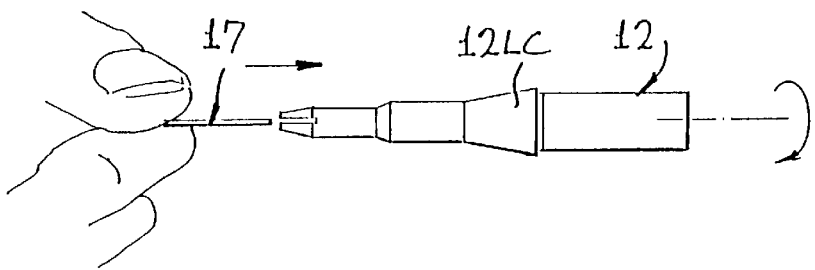

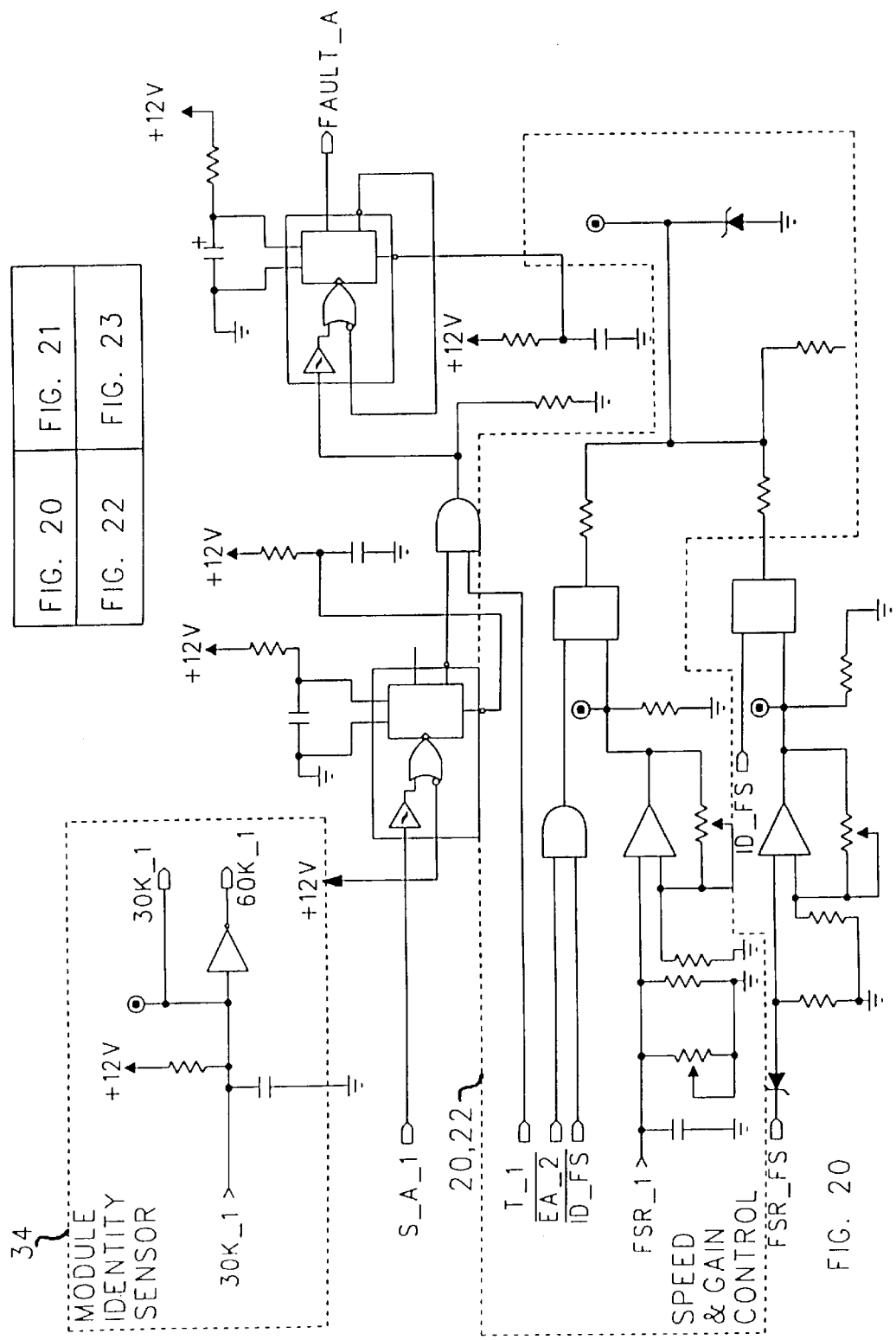

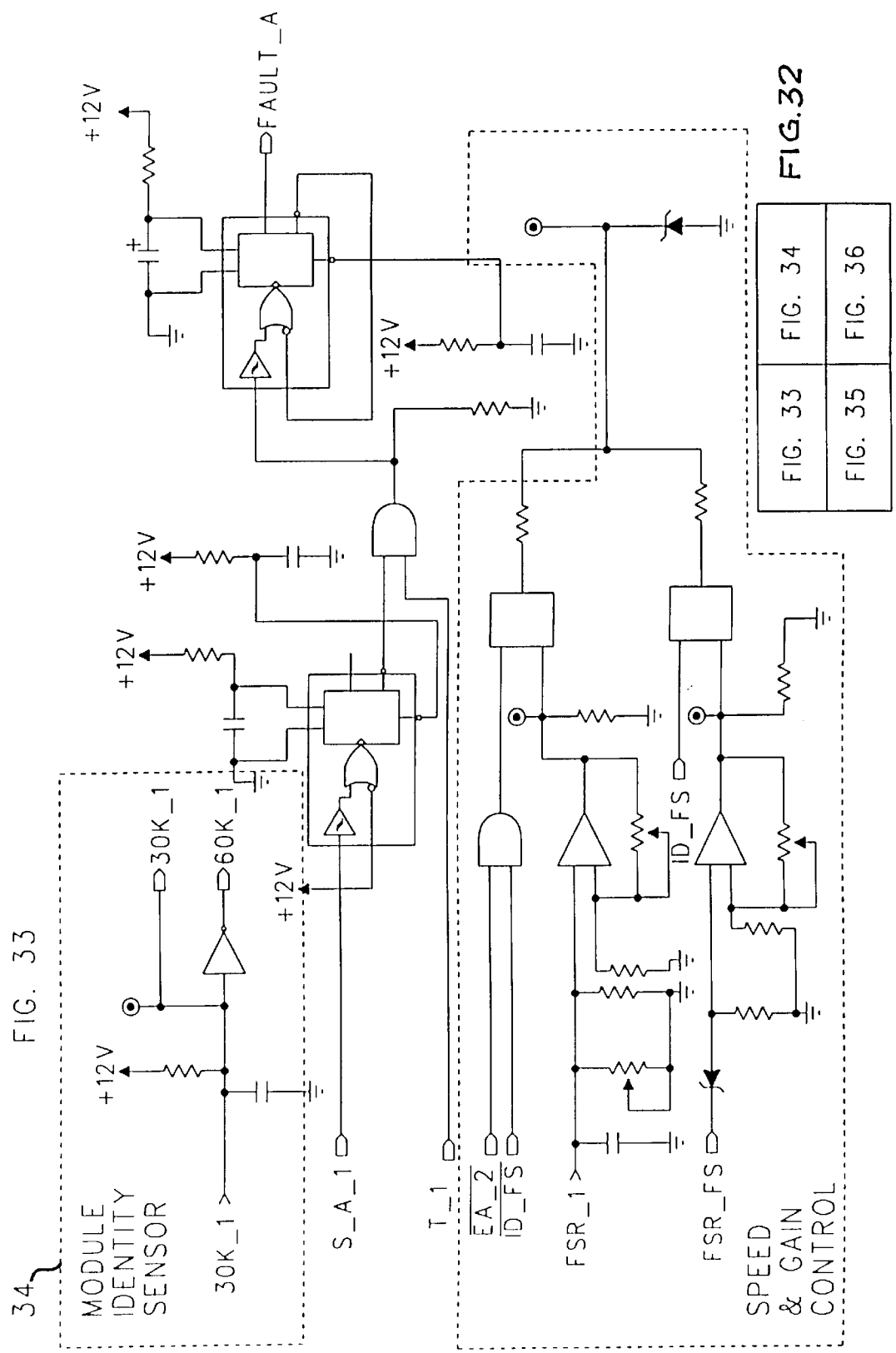

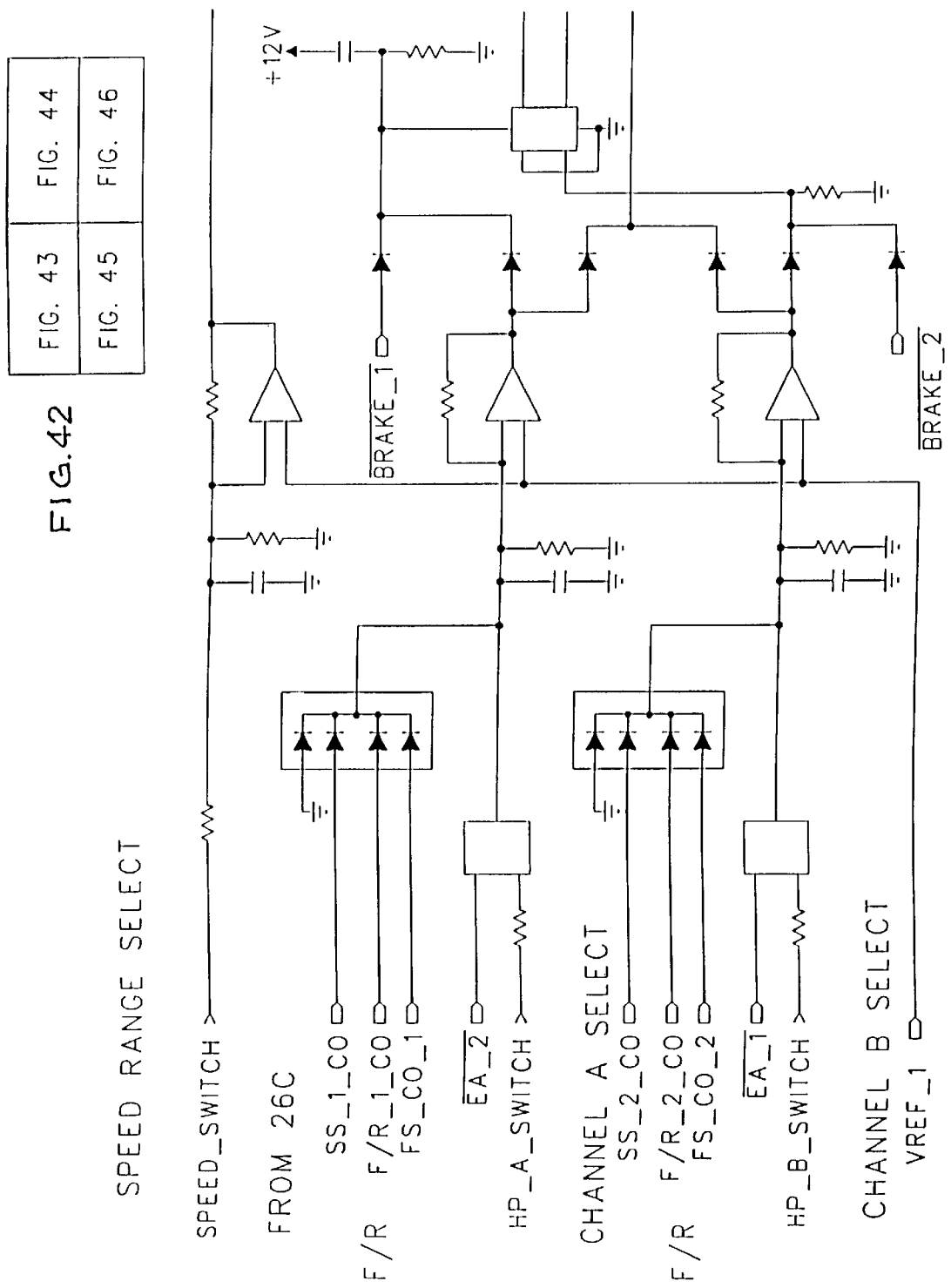

ated May 1, 1997, now non provisional application Ser. No. 09/069, 349, filed Apr. 29, 1998.

ELECTRONIC CONTROLLED SURGICAL POWER TOOL

REFERENCE TO RELATED APPLICATIONS

This is a non-provisional patent application based upon provisional patent application Ser. No. 60/045,249 filed May 1, 1997, now non provisional application Ser. No. 09/069, 349, filed Apr. 29, 1998.

Tools employed in carrying out this invention are the subject of provisional patent application Ser. No. 60/045,246 filed May 1, 1997, and provisional application Ser. No. 60/045,250 filed May 1, 1997, now non provisional application Ser. Nos. 09/069,342and 09/069,474, filed Apr. 29, 1998 and Apr. 29, 1998 respectively, the contents of which application are incorporated by reference.

BACKGROUND OF THE INVENTION

The present invention relates to a surgical power control system for controlling the operation of a plurality of surgical tools such as drills, burs and saws. Such power systems are known but are not as convenient to use as would be desirable. Such systems consist of a control unit, a hand held unit which accommodates various tools, various plug-in tools, foot operated controls and the necessary interconnections.

One basic objective of those who supply such surgical control systems is to provide a system which is as easy and responsive as possible for a surgeon to use. A significant disadvantage of systems now on the market is that the speed control for drills, saws, etc. is effected by means of a manually operated lever on the handpiece. Such a lever may require use of a second hand to effect speed changes. This is obviously not convenient and may cause some delays in an ongoing surgical procedure.

Typical of prior art powered surgical tool systems are those disclosed in the following patents:

| | | | |
|---|---|---|---|
| 4,827,615 | G. S. Graham | May 9, 1989 | MICROSURGERY SAW DRIVE |
| 5,115,175 | H. H. Fletcher | May 19, 1992 | DRILL HAVING ALTERNATE MODE CONTROL |
| 4,653,338 | H. D. Yeomans | Mar. 31, 1987 | APPARATUS FOR DRIVING A MEMBER |
| 5,201,749 | Sachse et al | Apr. 13, 1993 | CIRCULARLY OSCILLATING SAW |

BRIEF DESCRIPTION OF THE INVENTION

The surgical power control system of the present invention has a number of advantages. One is that a hand held motor unit is provided which includes integrated force sensitive control surfaces which provide speed control and virtually all needed controls, each operated by finger pressure of the same hand that holds the motor and tool holding assembly. Thus, rather than having a control speed of a saw or a drill by operating a lever or a foot pedal, the surgeon simply presses or squeezes a plate on the hand held motor unit to change speed, to change the speed range, or to reverse the direction of the motor.

Another significant advantage of the surgical power control system of the present invention is that certain control functions are automatically established by inserting a tool into the hand held motor unit. The motor unit includes a "Hall effect" or magnetic field responsive component which responds to the detection of the magnetic fields produced by permanent magnets in the various tool modules as they are plugged into the motor unit. This feature insures that the motor is only operated in the appropriate range for the tool module selected.

Other features of the handpiece include:
  The brushless DC motor integrates advanced materials and design technology to deliver exceptional power at all speeds.
  Ergonomic shape provides exceptional control and sensory feedback.
  Advanced electronic circuitry brakes motor speed instantaneously.
  Pressure sensitive surfaces control variable speed, maximum speed range, and motor direction and "SAFETY" modes.
  The Motor Unit operates in both high speed (0–70,000 RPM) and standard speed (0–25,000 RPM) modes.
  Lightweight integrated power cord.
  Internal module coupling mechanism allows easy and quick insertion of a wide variety of Handpiece Modules.
  All Handpiece Modules can be inserted into the Motor Unit in four different orientations at 90-degree intervals.
  Insulating thermoplastic housing assures cool handpiece operation and extremely high durability.
Motor unit and cord are sealed and fully autoclavable.
  The motor unit of the system includes other features, such as:
  allowing for hand control of variable speed, maximum speed range,
  Forward/Reverse, and
  "SAFETY" mode operation.
Other advantages of the power control console of this system include:
  Two handpiece ports allow sequential dual handpiece operation.
  Speed range and Forward/Reverse controls.
  LED speed range indicator scaled for 25%, 50%, 75% and 100% of maximum motor speed.
  Audio voice circuitry provides speed range and safety mode verification announcements.
  Flashing "A" or "B" LEDs indicates that the system is in the "SAFETY" mode.
  Repeating audible beep indicates Reverse operation.
  Positive-lock cord connectors for positive actuation and durability.
  Footswitch control port on back panel for alternative foot switch or hand switch control.
  Irrigation system control port on back panel.
  Universal power supply provides over 260 Watts of peak power.
  A clear SPEED CONVERSION CHART affixed the to top of the Power Control Concert to identify selected module operating speed ranges.
  The low profile of the power control console enclosure fits most system utilization spaces.
  Hospital grade autoclavable handpiece and AC power cord.

BRIEF DESCRIPTION OF THE DRAWING

This invention may be more clearly understood with the following detailed description and by reference to the drawings in which:

FIG. 5 is an exploded view of the hand piece including motor unit, cord and sensor pad assembly;

FIGS. 6A, 6B and 6C are top plan, side, and bottom plan views of the semiconductor film assembly forming part of the sensor pad assembly of FIG. 5;

FIG. 6D is an enlargement (8:1) of Detail C of FIG. 6C;

FIG. 6E is an enlargement (8:1) of Detail E of FIG. 6C;

FIG. 7A is a front elevational view of a connector board including contacts for connecting the semiconductor film assembly of FIG. 6 to the electrical wires in the cord assembly of FIG. 5 with an enlarged detail, 16:1;

FIG. 7B is an enlargement (16:1) of the contact array of FIG. 7A;

FIG. 8 is an enlargement (16:1) of detail B of FIG. 7A;

FIG. 12-1 is a generally front perspective view of the power control console of this invention;

FIG. 12-2 is a generally rear perspective view of the power control console of FIG. 12-1;

FIG. 12-3 is a rear perspective view of the power control console of FIG. 12-2 with cords in place;

FIG. 12-4 is a fragmentary front view of the front of the power control console with a cord in the process of being inserted into the A connector port of the power control console of FIGS. 11 and 12;

FIG. 13 is a side elevational view of the straight driver of this invention with a burr in place;

FIG. 14 is a side elevational view of the bur of FIG. 13 showing its head and its unique bur shank detail;

FIG. 15 is a side elevational view of the collet of the drill module of FIG. 13 with an arrow illustrating the direction for turning the collet to secure the bur of FIG. 14 in place in the module;

FIG. 16 is a side elevational view of the locking collar of the module of FIG. 13 with the arrow denoting the clockwise rotation of the locking collar for bur insertion;

FIG. 17 is a side elevational view of the process of bur insertion;

FIG. 18 is a side elevational view of the process of bur removal;

FIG. 19 is a layout diagram of drawings FIGS. 20–23 which constitute the electronic schematic of the processor for input signals from the handpiece and the control panel to channel A;

FIGS. 20 through 51 and their subordinate component drawings constitute the electronic schematic drawings of the system of FIG. 1, namely;

FIG. 24 is a layout diagram of drawings FIGS. 25–27 which constitute the motor control electrical schematic of the signal processing for channel A of this invention;

FIG. 28 is a layout diagram of drawings FIGS. 29–31 which constitutes the motor control electrical schematic of the signal processing for channel B of this invention and the same as the schematic for channel A;

FIG. 32 is a layout diagram of drawings FIGS. 33–36 which constitutes the electronic schematic of the processor for input signals from the handpiece and toe control panel to channel B and the same as for channel A;

FIG. 37 is a layout diagram of drawings FIGS. 38–41 which constitute a schematic drawing for a footswitch of this system;

FIG. 42 is a layout diagram of drawings FIGS. 43–46 which constitute a schematic for the face panel controls of the power control console of this invention; and FIG. 47 is a layout diagram of drawings FIGS. 48–51, which constitute a continuation of the face panel controls of the power control console of this invention.

DETAILED DESCRIPTION OF THE INVENTION

Overall System Operation

Figure 1:
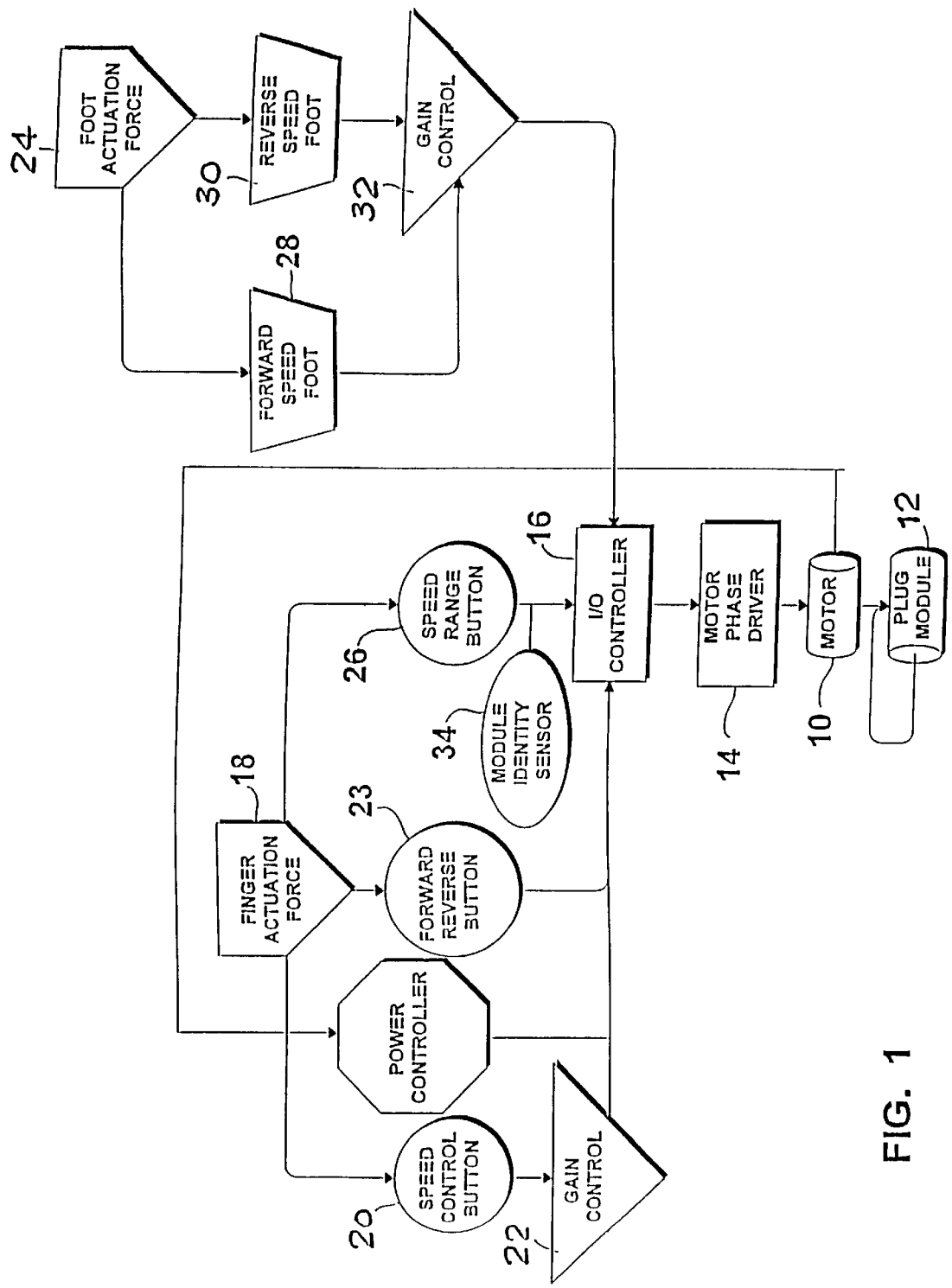
FIG. 1 is block diagram showing the principal functions of our surgical power control system.
Figure 1A:
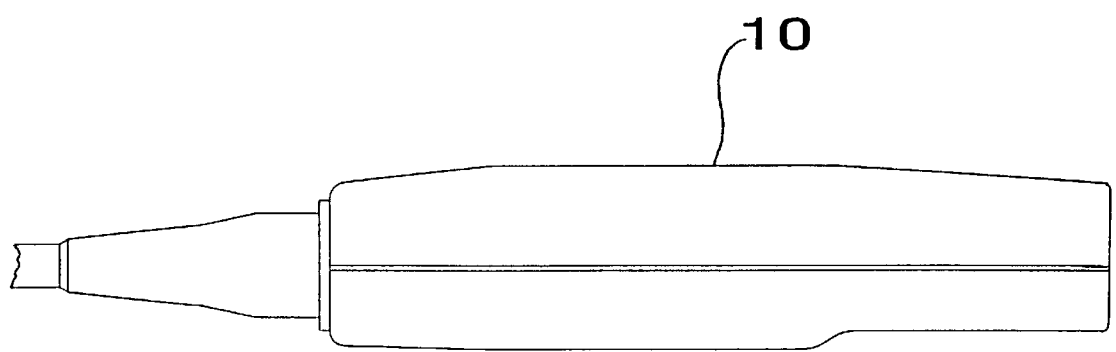
FIG. 1A is a side elevational view of the hand held motor unit of this invention.
Figure 10:
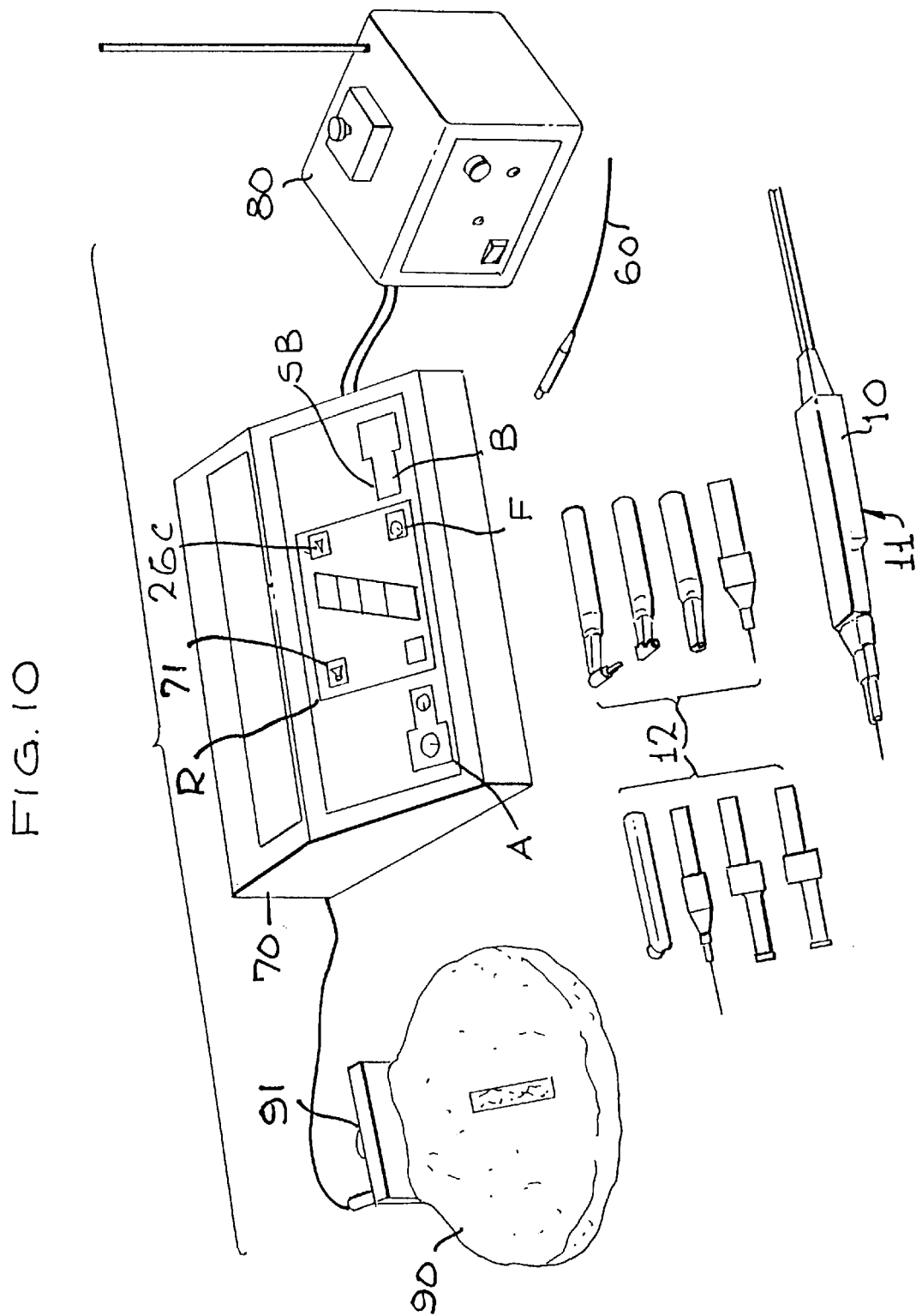
FIG. 10 is the reproduction of a photograph showing the system of this invention including the Power Control unit, a footswitch, an irrigation console a motor unit, a handpiece module, cords and eight surgical power tools.
Figure 10A:
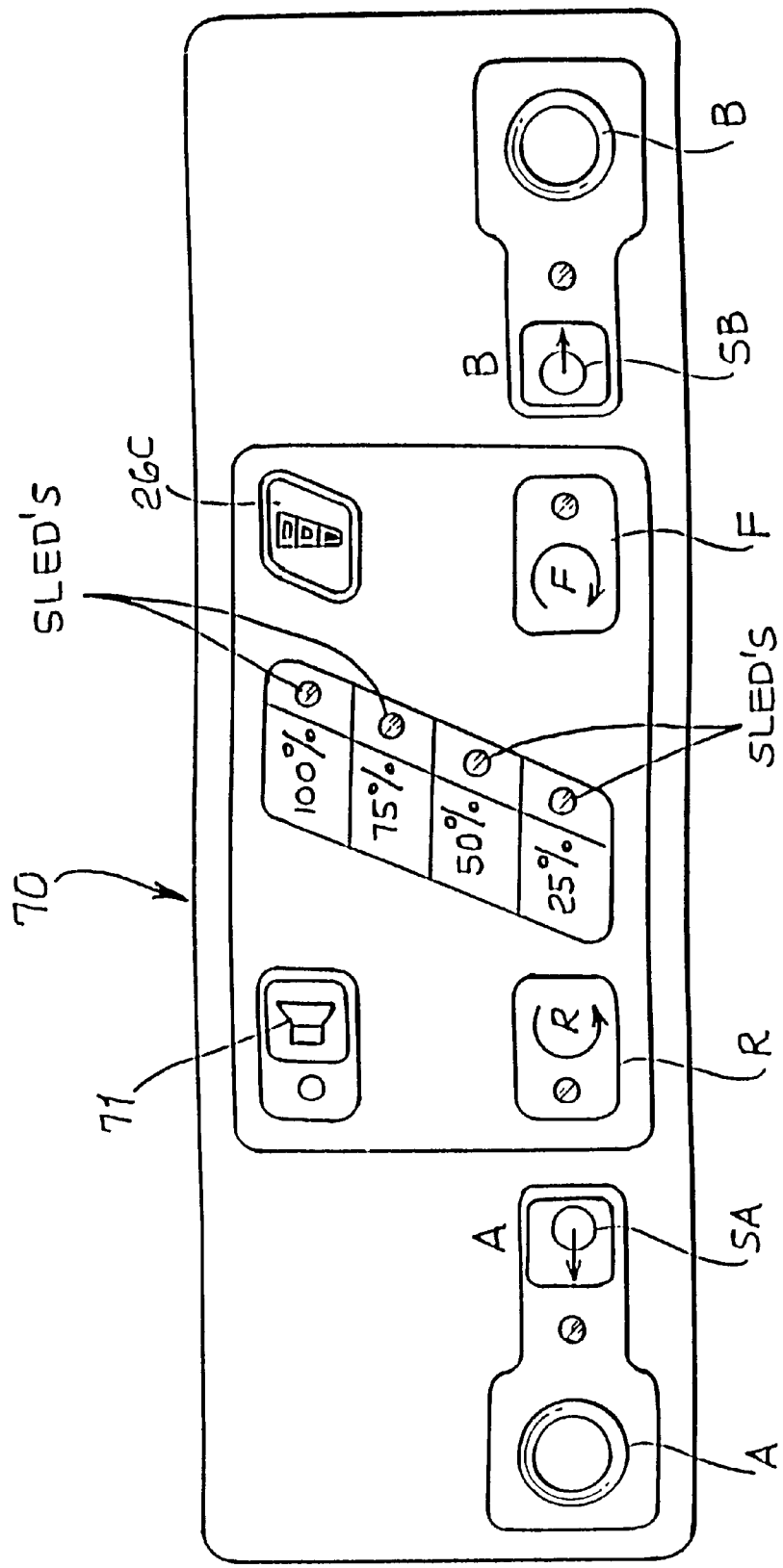
FIG. 10A is a front elevational view of the power control console faceplate and its controls.

The surgical power control system of the present invention may be best understood by first reviewing the system from the standpoint of the surgeon with the controls available to him and their functions best illustrated in FIG. 1, in combination with FIGS. 10 and 10A. It is a system for controlling the speed of an electric motor 10 capable of driving any of a number of plug-in modules 12, which include tools such as drills, burs or saws. A series of representative modules are shown in FIG. 10 and certain of which are more fully disclosed in the above referenced patent application, the controls of which are incorporated by reference herein. The motor 10 is a part of a handpiece 11 of FIGS. 1A–8 and 10 and is capable of selected speeds as high as 70,000 RPM when driven by a motor phase driver 14 of FIG. 1 which in turn is under the control of an input/output controller 16. The hand piece 11 also includes a finger pressure operated speed controller 18 of FIGS. 2–4 and 6, to provide speed and direction of the motor 10 as well as a SAFETY, motor OFF positions.

The Handheld Motor and Control Unit

The surgeon operating the system has a number of choices of inputs. He may provide a speed input signal by applying force to the pressure sensitive variable speed control sensor 20 of FIGS. 2–4 and 9 which is represented in FIG. 1 by the block "Finger Actuation Force" 18. This provides a force represented as the "Speed Control Button" 20, the output of which is an electrical sign and the gain of which is controlled by a gain control circuit 22 with output supplied to the input-output controller 16. A speed range selection may also be by a control represented in FIG. 1, button 26 on FIGS. 10 and 2–8 and again as pressure sensitive region 26 of FIGS. 2, 3, and 4 so that the speed range produced by the finger actuation force 18 of FIG. 1 may be over a full range of, for example, 0–70,000 rpm, or 0–50,000 rpm or 0–25,000 rpm depending upon which range has been selected by the surgeon.

As indicated above, the hand held motor unit 11 also includes a forward/reverse sensor 23 of FIGS. 2–8 which corresponds to a forward/reverse button 23 of FIG. 1, the output of which is supplied to controller 16 of FIG. 1 to control the direction of rotation of the motor 10. The net result of the presence of this handheld motor unit 10 is that the surgeon has at his fingertips, all controls for performing the various procedures requiring selected tool modules. Visual attention is directed toward the patient and not toward the power source. Audio indications of any speed range change are provided to the surgeon without any need to lift his eyes from the procedure at hand.

Any command of reversal of motor direction is also indicated aurally to the surgeon to avoid any unintended change of motor direction. The operating speed of any module 12 is within its appropriate range only, owing to the presence of Hall effect detector in the handpiece 11 and control circuitry, which identifies the module in place.

Change of speed within the working range is the result of mere change in pressure of the surgeon's fingers or thumb on the pressure sensitive on-surface control of the handpiece. All different control options are arranged in a straight line for easy tactile identification. The variable speed control sensor 20 is located at the outermost and narrower end of the handpiece 11 where it is easily identified tactually and tapered corresponding to speed from the widest (fastest speed within the range) to the narrowest (slowest speed within the selected range). Of even greater importance, increasing thumb or finger pressure on the sensor increases the longitudinal pressure area on the sensor 20 thereby increasing the speed of the motor 10 providing a natural motion and an appropriate system reaction. Finger pressure at any point along the length of the sensor pad 20 will produce motor speed control. There is no mechanical lever present and the ergonomic design is more comfortable, less tiring and has minimum visual interference with the procedure at hand.

Motor direction is controlled by the forward/reverse section 23 of the sensor pad. By depressing this sensor, motor direction is reversed. A repeating audible "beep" sounds from the power control console of FIG. 10 during reverse operation and the reverse LED on the power control console is illuminated. The default mode of operation of the system upon powering up by operating the ON/OFF AC power switch of the power control console of FIG. 10, the system is operational in the FORWARD direction at the LOWEST speed range.

The SAFETY position of the pressure sensitive sensor which disables the motor 10 operation until released by a second application of pressure, is located at the opposite end of the force sensitive sensor for easy identification.

The integrated force sensitive controls 18, 20, 23, 26, and SAFETY, discussed above, are built-in low travel switches which, when pressure is applied, become more conductive. This is enclosed by a semi-rigid cover plate with flexure characteristics compatible with natural finger actuation pressure. The internal switch operators as best seen in FIGS. 5–8 include a textured semiconductive film or surface coating 48–50 which, when pressure is applied through the cover plate 52, engages the underlying conducting area. The additional conducting surface area translates to greater conductivity as a result of actuation pressure. This increased conductivity when applied to areas 48 and 49 provide a switching operation; constitutes a signal for increased motor speed or a command when applied to area 50 and when the pressure is applied to a different designated area of the force sensitive control surface.

As a companion feature of this system, the handpiece 11 includes a radiation detector 34 such as a Hall effect device adjacent to the tool module chucking device for each of the various modules 12, which are designed for use in this system. The detector 34 responds to the unique signature of any module, e.g. magnetic field, its presence or absence, field strength or polarity from a magnet embedded in the shank of the module. The detected signal is used to control the operation of the system with that module in place, e.g. limiting the operating speed. In its basic form, the presence of a module carrying a magnet, signals a speed limited tool while the chucking of any other tool without a magnet present, allows speeds up to the system limit, e.g., 70,000 rpm to be used. The actual speed from 0 rpm to the speed range limit it is controlled by the magnitude of finger pressure applied to control 20.

The hand held motor unit of FIGS. 1A–10 includes in addition to motor 10, a magnetic field sensor 34 which senses a magnetic field produced by a magnet in whichever of modules 12 is plugged into the motor unit. Each tool module 12 contains a magnet having its own signature strength and polarity so that the magnetic field sensor 34 can identify which module is plugged into the motor unit 10. This is important because some tools may be permitted to operate at high speeds and others may be limited to lower speeds. The result of operation of this sensor is that no module may be operated outside of its designated speed range.

In FIG. 1 the "Module Identity Sensor" (Hall effect sensor) 34, is shown connected to controller 16 along with the input from the speed range button 26 signal since both operate to limit the speed range which can be selected. Thus, one may operate a bur at a high speed such as 70,000 rpm and when a module containing a saw is plugged into the motor unit, the controller 16 is then empowered to limit the motor 10 to a lower rpm value.

Figure 2:
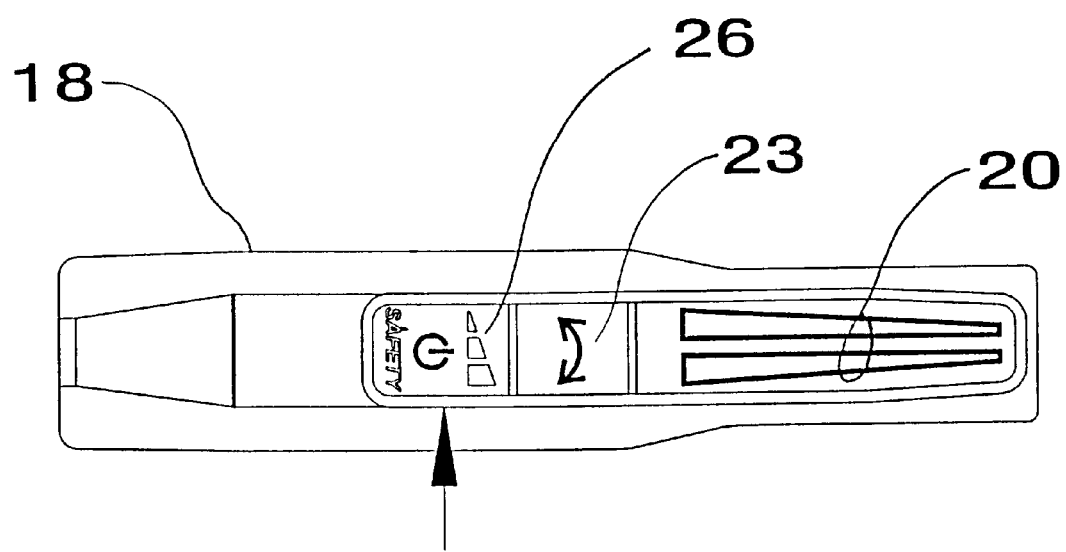
FIG. 2 is a top view of the sensor pad of the hand held motor unit with an arrow indicating a "safety" setting.
Figure 3:
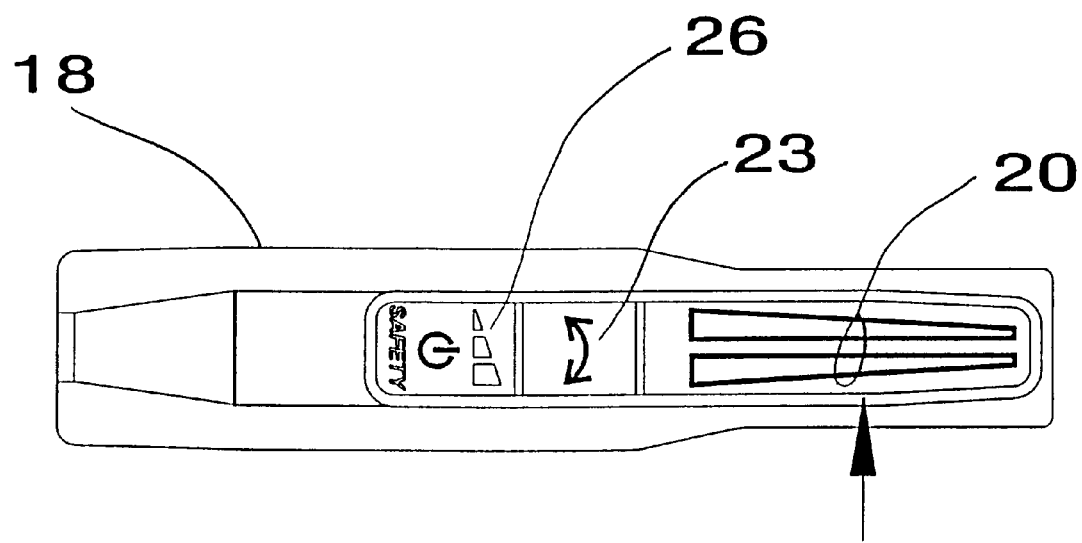
FIG. 3 is a top view of the sensor pad of FIG. 2 with an arrow indicating the variable speed control portion of the sensor pad.
Figure 4:
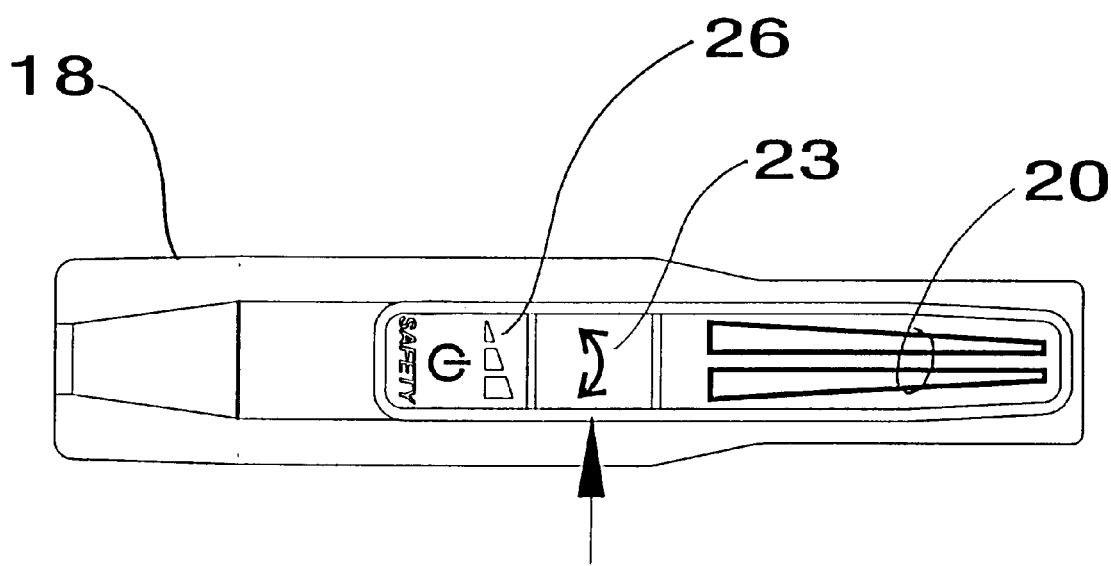
FIG. 4 is a top view of the sensor pad of FIGS. 2 and 3 with an arrow indicating the forward/reverse section of the sensor pad.

FIGS. 2, 3 and 4 are plan views of the handpiece cover plate which is part of the variable speed sensor pad incorporated into the hand held motor unit 11. By pressing this handpiece at the locations indicated by the arrow in FIG. 2, the surgeon can put the system in the SAFETY mode in which the motor is not operable or in an operating mode.

The actual motor speed is selected by the surgeon's act of pressing the area 20 as indicated by the arrow in FIG. 3. The speed range is set by pressure at area 26. Each successive finger pressure application selects a higher speed range to the speed range limit and then to the lowest range.

The selection of forward or reverse motor direction is designated by pressing the area 23 once indicated by the arrow in FIG. 4. A second application of finger pressure to the same area 20 returns the operating direction to the previous state. Whenever, the reverse mode has been set, the audio portion of the power control console provides an audio indication of repeating "beeps."

FIG. 5 is an exploded view of the motor unit and finger actuation force sensor assembly, given the numeral 40, including a lower half body 42, an upper half body 44, a motor 10 and cable assembly 46, semiconductor/adhesive film members 48, 49, and 50 and a handpiece cover plate 52 which is an edge or side view of the handpiece shown in FIGS. 2, and 3. The semiconductor members 48, 49. and 50 are adhesively attached to a depression or cavity 54 formed in upper half body 44.

FIGS. 6A, 6B and 6C show details of the semiconductor film members 48, 49 and 50 which are secured to surface 54 of upper body half 44 of FIG. 5. Also positioned in this surface is a small depression or cavity 56, which receives the Hall effect sensor 34 of FIG. 1. The Hall effect sensor 34 is connected via the hand unit power cord to the power control console, best seen in FIG. 10 for automatic speed range selection in response to the module detected.

Members 48, 49, and 50 of FIGS. 5–8, specifically, are electrically connected to a connector board 58 which is shown in FIG. 5 and in greater detail in FIGS. 7 and 8 and which provides interconnections between semiconductor film members 48, 49, and 50 and the Hall effect sensor 34; and conductors in cable 60 to the power control console 70 of FIG. 10.

In FIGS. 6A and C and their enlarged details C and E, the three separate sets of interleaved fingers of electrical switch conductors are visible, particularly in the enlarged detail E shown in an 8:1 magnified size as compared to FIG. 6A. The underside of the board of the variable resistance networks 48,49 and 50 may be seen in FIG. 6C its conductors to the connector board 58. The thin nature of the assembly of the networks is illustrated in FIG. 6B. The details of the connector board 58 are shown in FIGS. 7 and 8 including details A and B and two rows of contacts 581 and 582.

Suffice it to say, pressure applied to each of these three sections 48, 49 and 50 by its semiconductive cover produces a change in resistance, which is detected at the control console as a signal or command from the handheld unit 11. Depression of the flexible external wall portion 52 of FIGS. 2–5 above sections 48 and 49 produces a conduction change which constitutes a switching operation, 0/1. Pressure on the elongated section 50 will change the resistance as a function of the pressure applied, greater pressure by a finger on the flexible outer wall of housing, plate 52, will make a greater change (reduction) in resistance across section 50 which is interpreted as a command for greater speed and the system under the command from the power control console of FIG. 10, responds to increase the power applied to the motor 10 and the speed of the motor and the surgical tool increases. As pressure is released the motor reduces in speed to a threshold where the circuit is open and the motor stops. The control console provides electrical dynamic braking for near instantaneous stopping after pressure release at the handheld unit.

Figure 9:
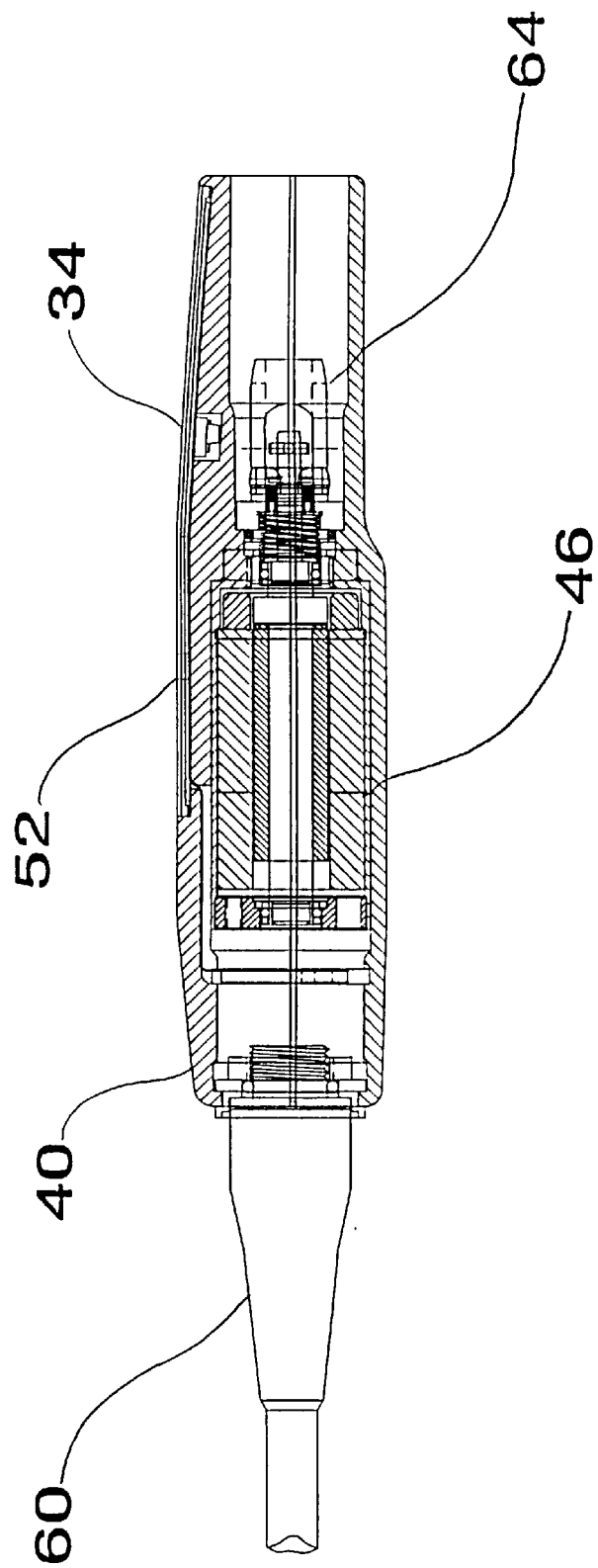
FIG. 9 is a sectional view through the hand piece of FIG. 5 showing the motor, motor output shaft, and magnetic field sensor (Hall effect sensor) used to identify which of the several tool modules are connected to the motor output shaft.

FIG. 9 is a longitudinal sectional view of the assembled hand held motor unit 40 including the cable 60, motor 46, cover plate 52, and Hall effect sensor 34. Connected to the output shaft of motor 46 is a drive member or chuck 64 which mates with the several tool modules 12. When the modules 12 are plugged into the motor unit 40 the magnets in the modules 12 are in close proximity to the Hall effect sensor 34 which generates an electrical signal to the input-output controller 16 of FIG. 1, identifying the module 12 to the controller 16. The controller 16, in turn, prevents the operation of the motor outside of the appropriate speed range for the module selected. Drive member 64 is configured to accept any of modules 12 in any of four orientations at 90° intervals.

The handpiece is enclosed and sealed within the body parts 4 and 44 as by sonic or adhesive welding of the parts 42 and 47. The cord 60 is likewise sealed to the hand piece 11 so that the entire handpiece 11, motor unit 10 and cord 20 are autoclavable.

The System

One entire system ready for installation and use is shown in FIG. 10 with its front panel showing in FIG. 10A. For a typical operating room installation, one power control console 70 is used with one irrigation control console 80, one or two hand pieces 11, each with their respective motor 10 for use with a variety of modules 12. One or more footswitches 90 with A/B selector switches 91 may be present for powering and controlling, any of the variety of modules 12. The line cord 60 of the handpiece 11 may be connected to either of the output ports A or B on the front of the power control console 70. The speed range selector button 26 of the handpiece 11 is duplicated as speed range selection switch 26C on console 70 and the forward/reverse control button 23 of the handpiece 11 is duplicated in finction by the forward F and reverse R switches on the front face of the console 70. Individual A and B selector switches SA and SB, corresponding to the port selector switch 91 of the footswitch 90. An audio control switch 71 controls the ON/OFF status of the audio features of the system such as audible voice announcing a speed change, motor reverse signal and the like.

The various speed ranges, 100%, 75%, 50% and 25% of the maximum motor speed are selected on the control panel of the control console 70 by speed range select, switch 26C of FIG. 10A and the current range is displayed on the face of the console with illuminated Speed LED's SLED next to each respective speed percentage label showing the present selected speed range.

Figure 11:
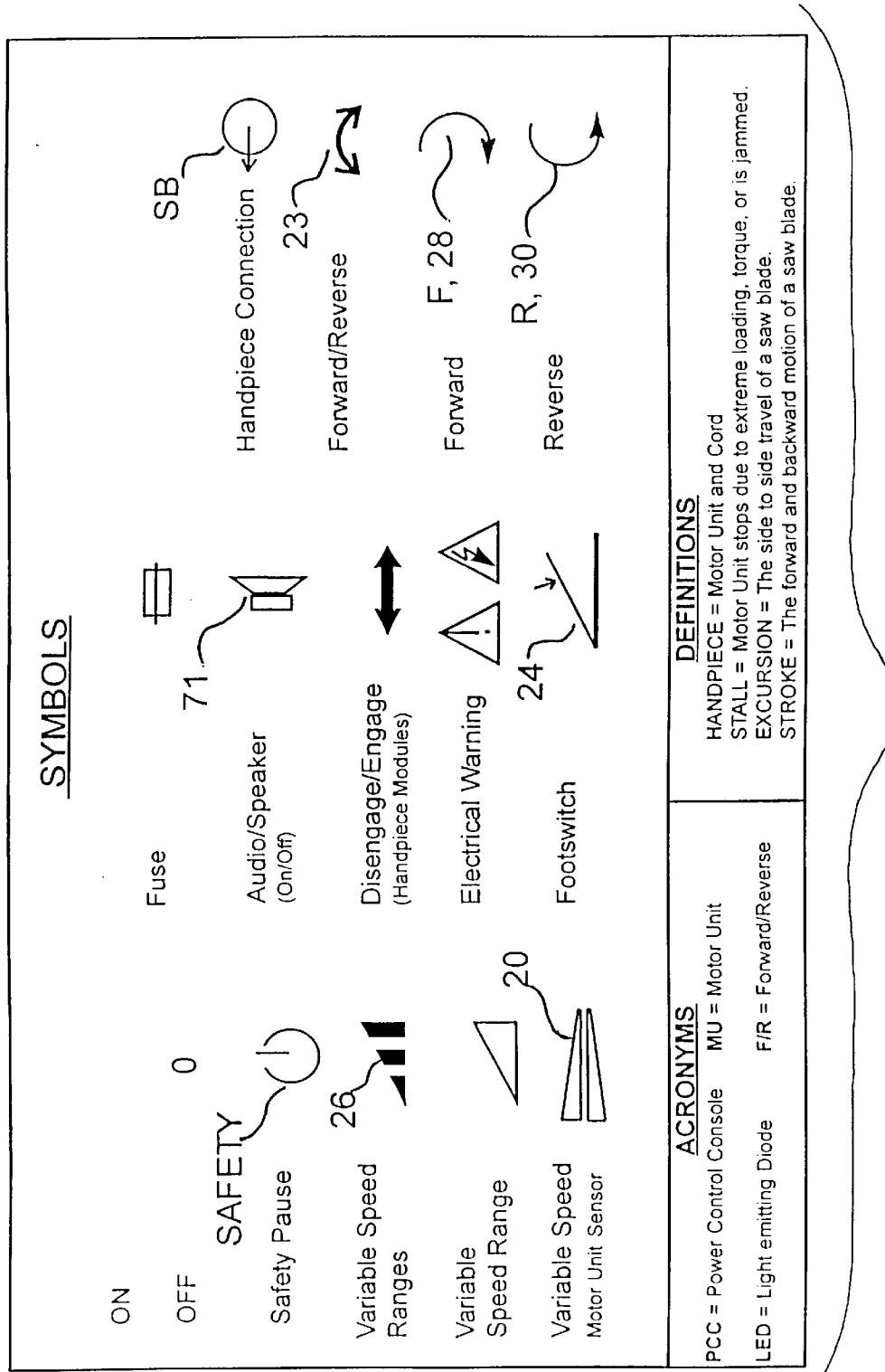
FIG. 11 is a symbol chart of the handset of this invention.

The various symbols used to denote various operating functions are shown in FIG. 11.

Figures 1, 12:
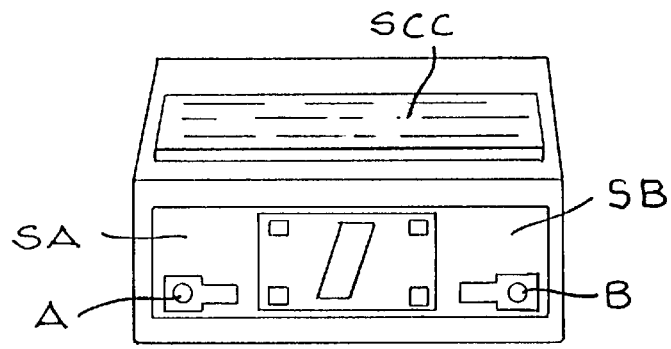
Figures 2, 12:
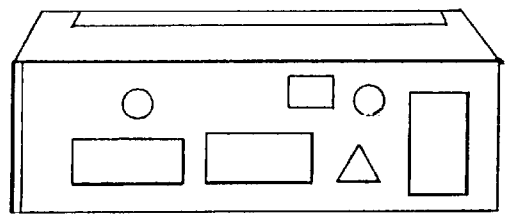
Figures 3, 12:
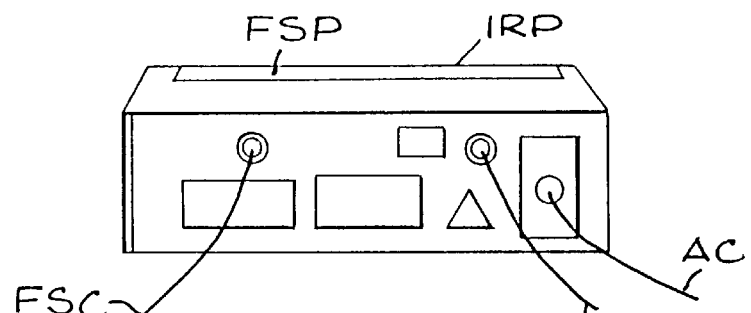
Figures 4, 12:
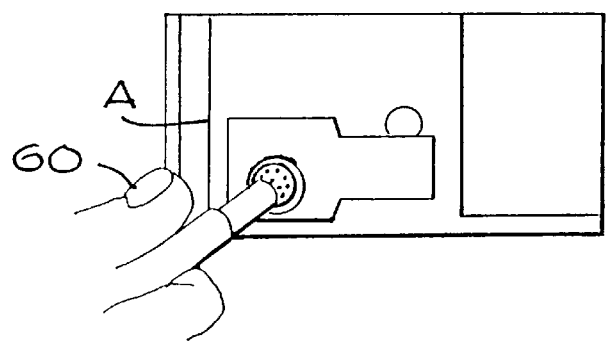
Figure 21:
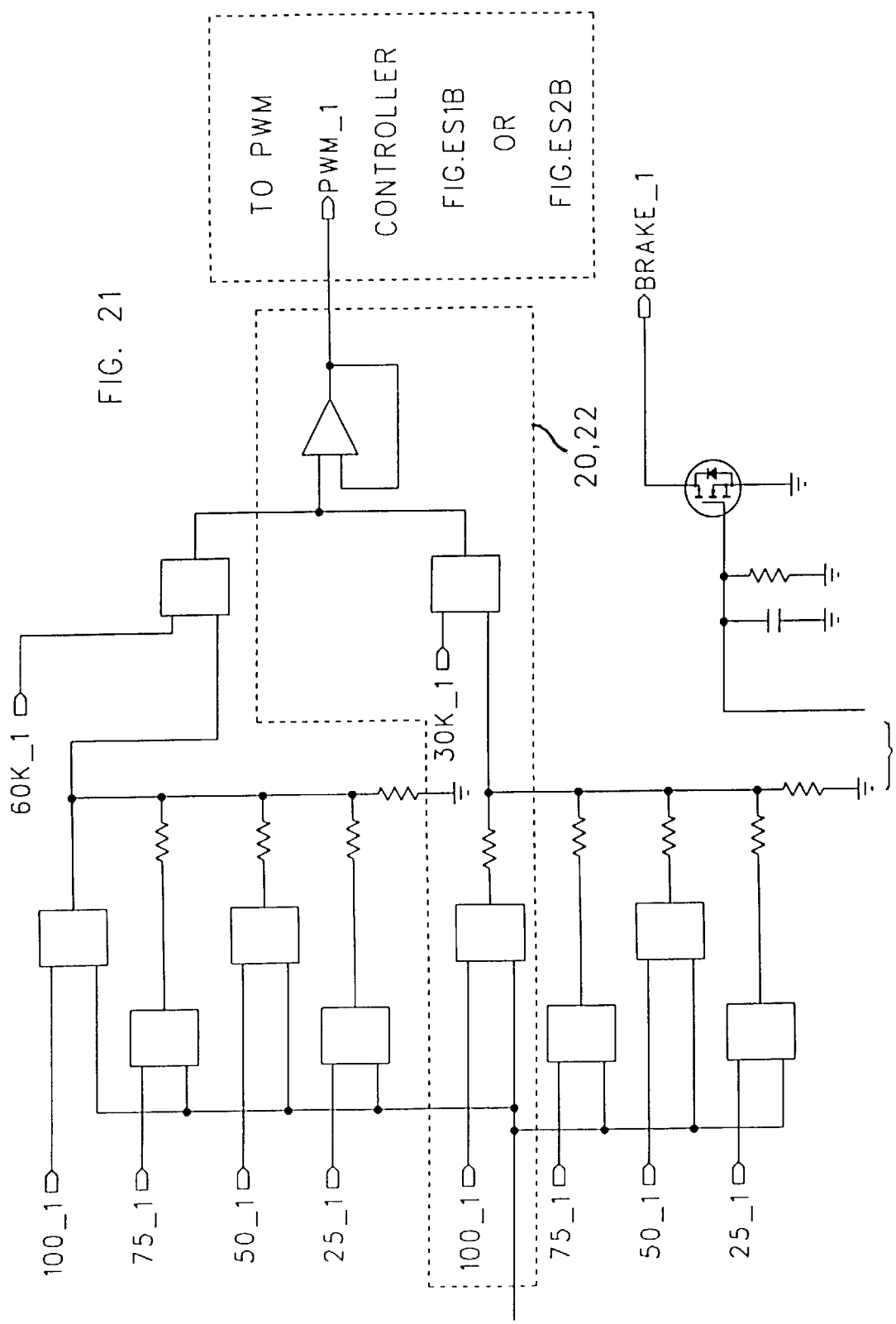

The details of the power control console 70 may also be better understood by reference to FIGS. 10A, 12-1 through 12-4. FIG. 12-1 shows the speed conversion chart SCC on the top front of the console 70 to assist the surgeon in verifying proper operating speeds for different modules 12.

The rear view of the console, found in FIGS. 12-2 and 12-3 show the rear controls and ports including the power switch, system power cord AC, the footswitch port FSP and footswitch cord FSC and the irrigation port IRP and its irrigation cord IRC. FIG. 12-4 shows the step of installing the cord 60 from the handpiece 11 into handpiece port A on the front of console 70.

The electronic circuitry incorporating the above functions and processes are detailed in the electrical schematic (ES) drawings FIGS. 19–51, to which reference is now made. The electrical schematic diagrams include each of the controls set forth in FIGS. 1 and 10 and provide each of the features described in this specification.

Figure 22:
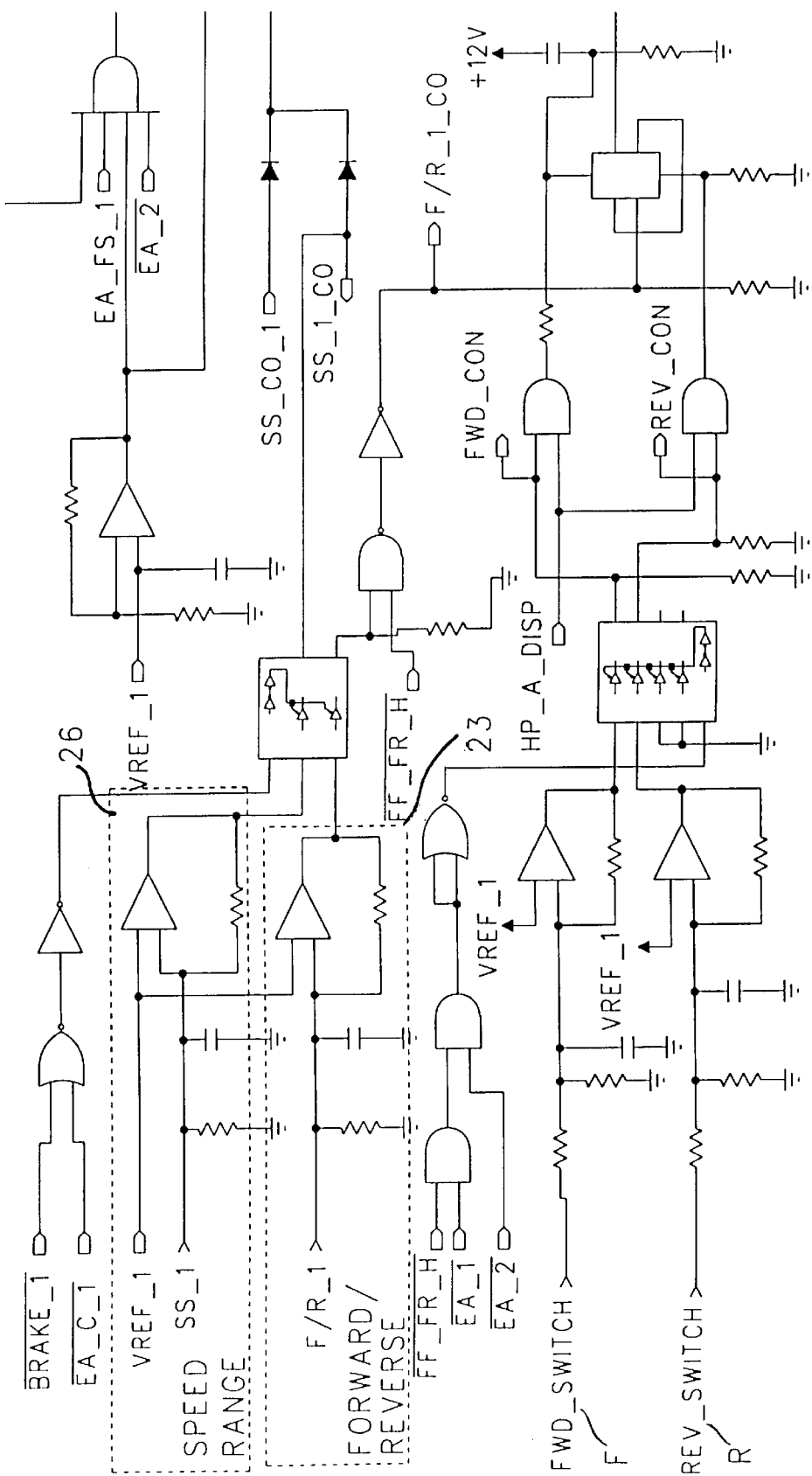
Figure 23:
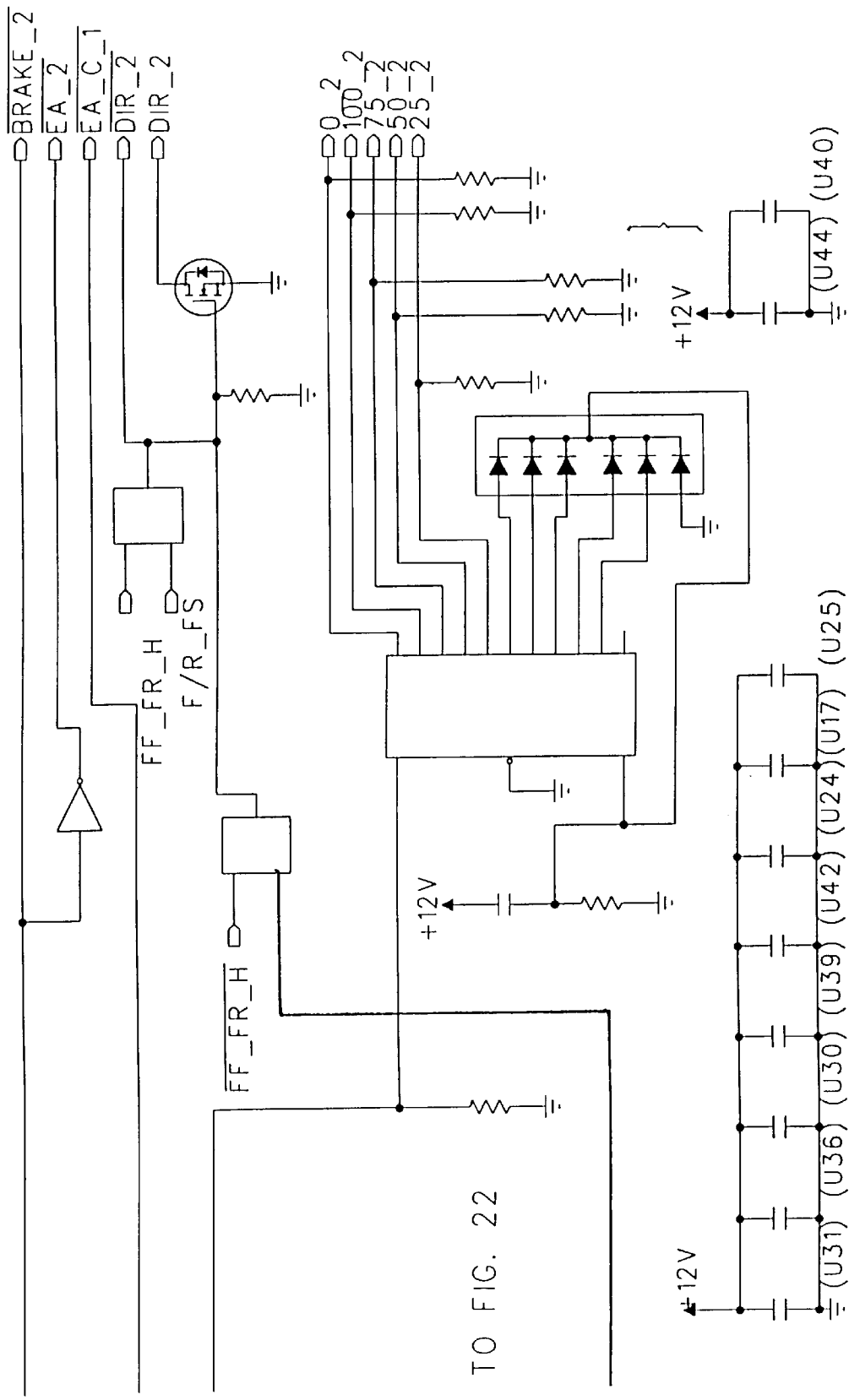

Referring now to FIGS. 20–23, the handpiece 11 controls for speed, range, direction and SAFETY represented by the finger actuation force block 18 of FIG. 1 for speed control 20, FORWARD/REVERSE direction control 23 and speed range selection 26 of FIG. 1 are all shown in FIGS. 20 and 22. The module identity sensor 34 block of FIG. 1 also appears in FIG. 20 and is connected to the speed control circuitry to prevent over speed operation of any modules 12 so detected in the module receiver of the handpiece 11.

Figure 25:
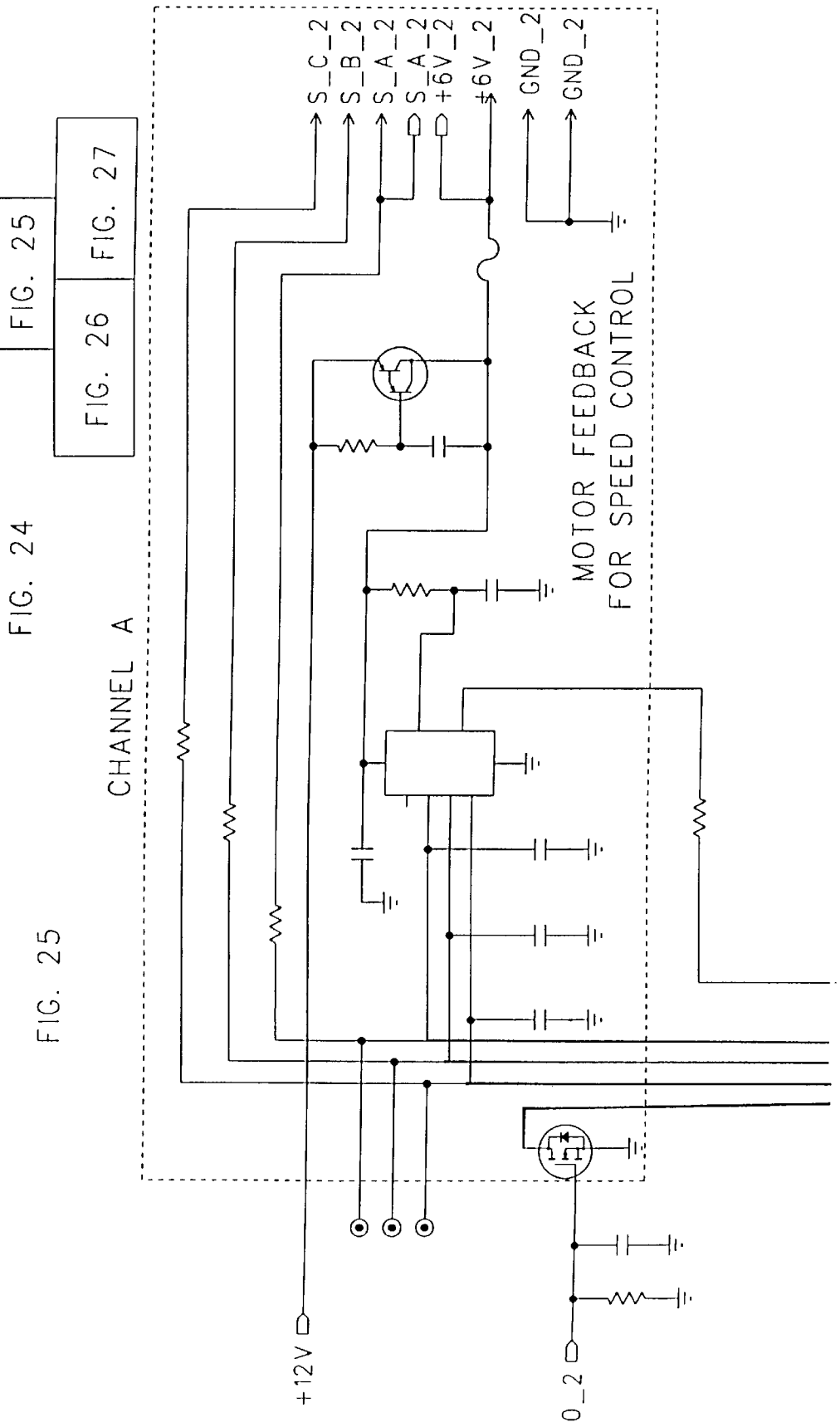
Figure 26:
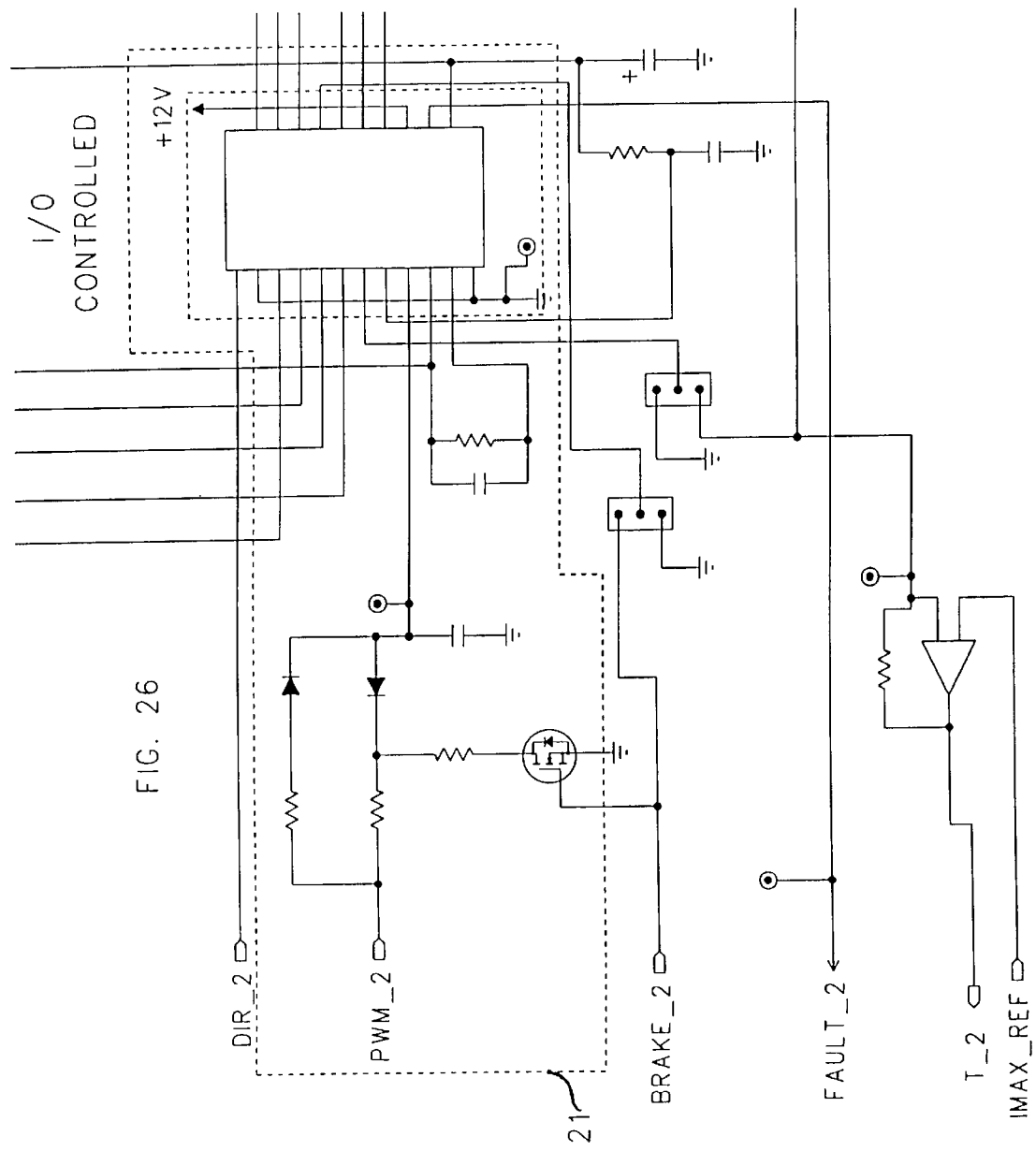
Figure 27:
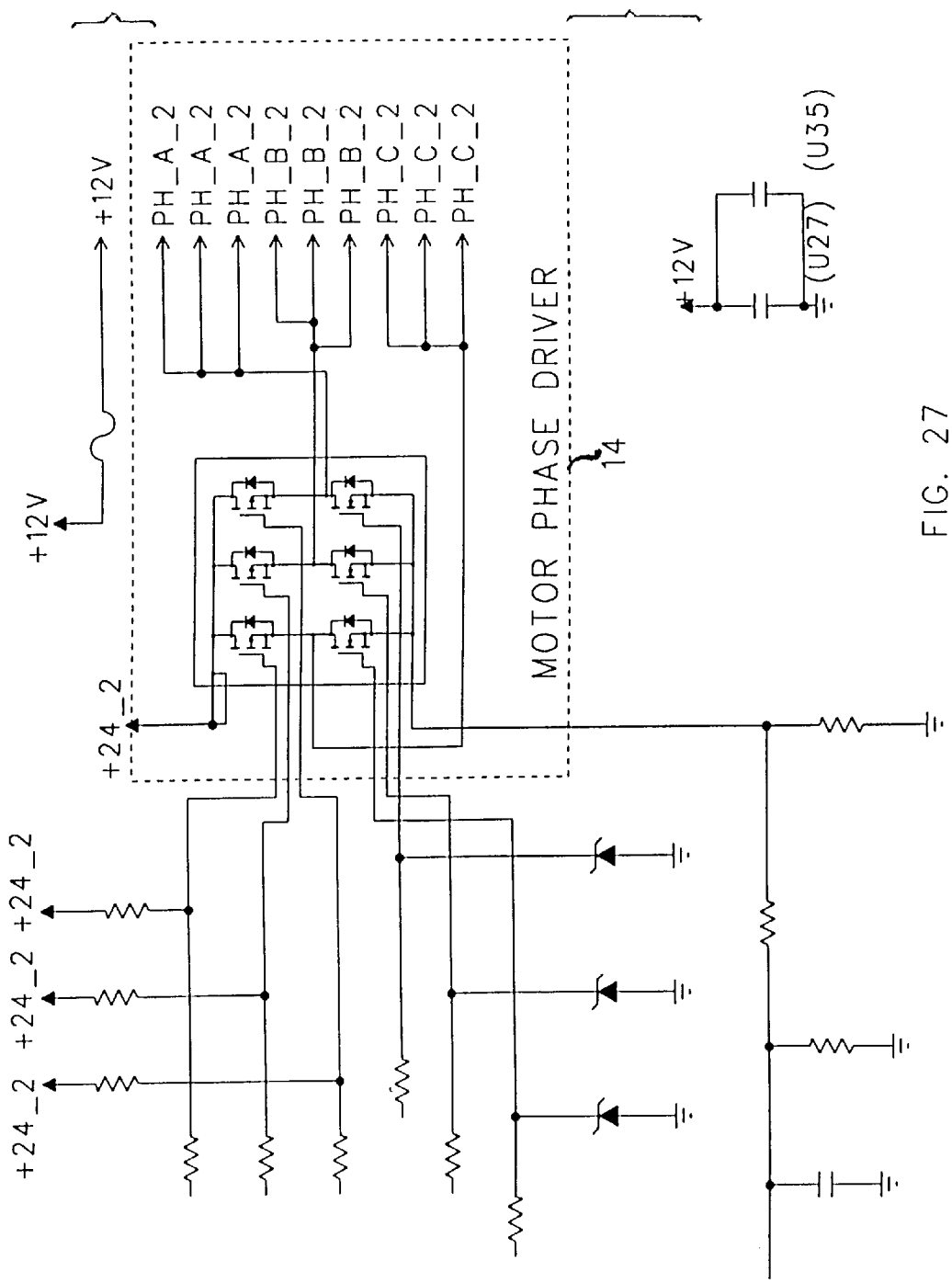

Further signal processing is carried out in the power control console 70 in the circuitry of FIGS. 25–27 for channel A. The pulse width modulator 21 and the input/output controller 16 of FIG. 1 appear in FIG. 26 while the motor feedback control circuit identified in FIG. 1 by the feedback conductor FB of FIG. 1 appears in FIG. 25. The motor phase driver 14 of FIG. 1 may be seen in FIG. 27.

Figure 29:
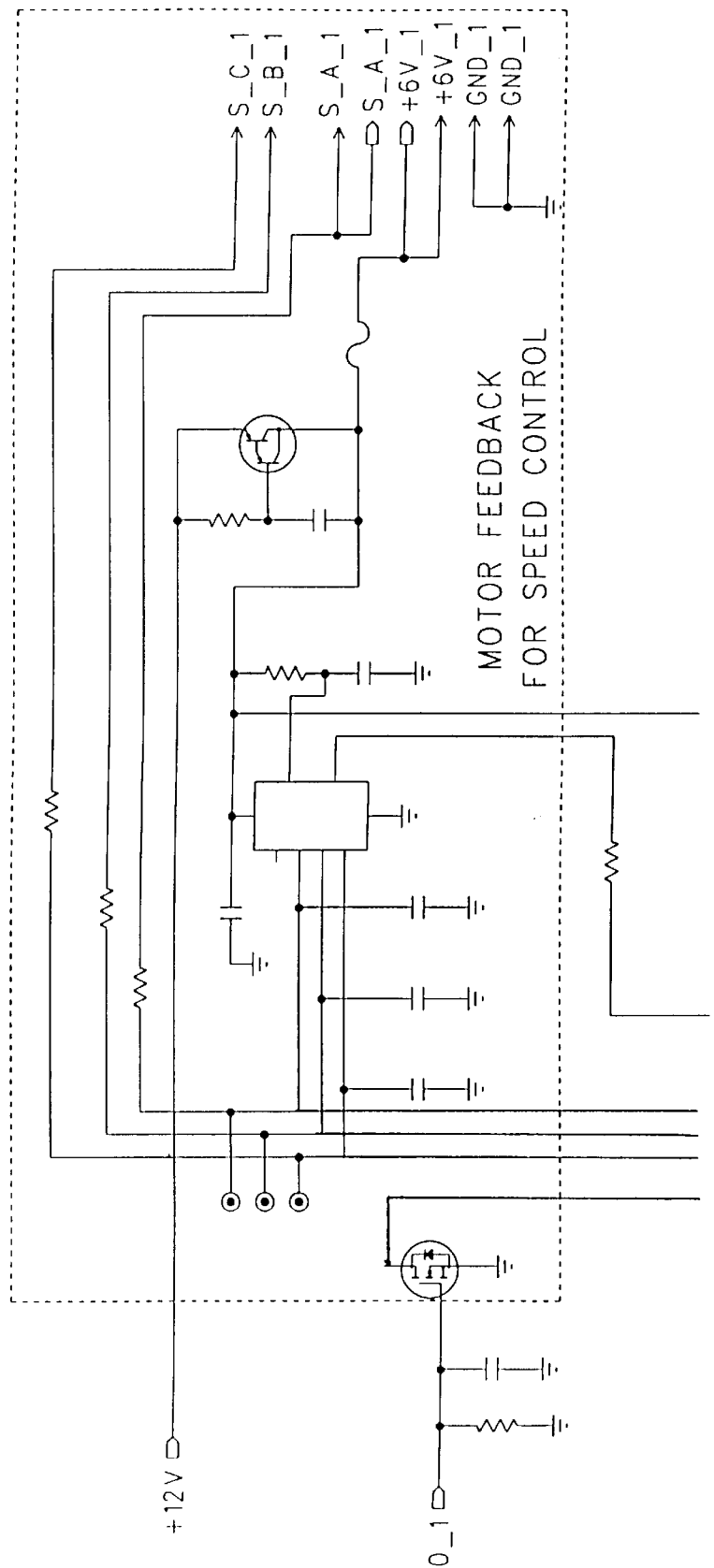
Figure 30:
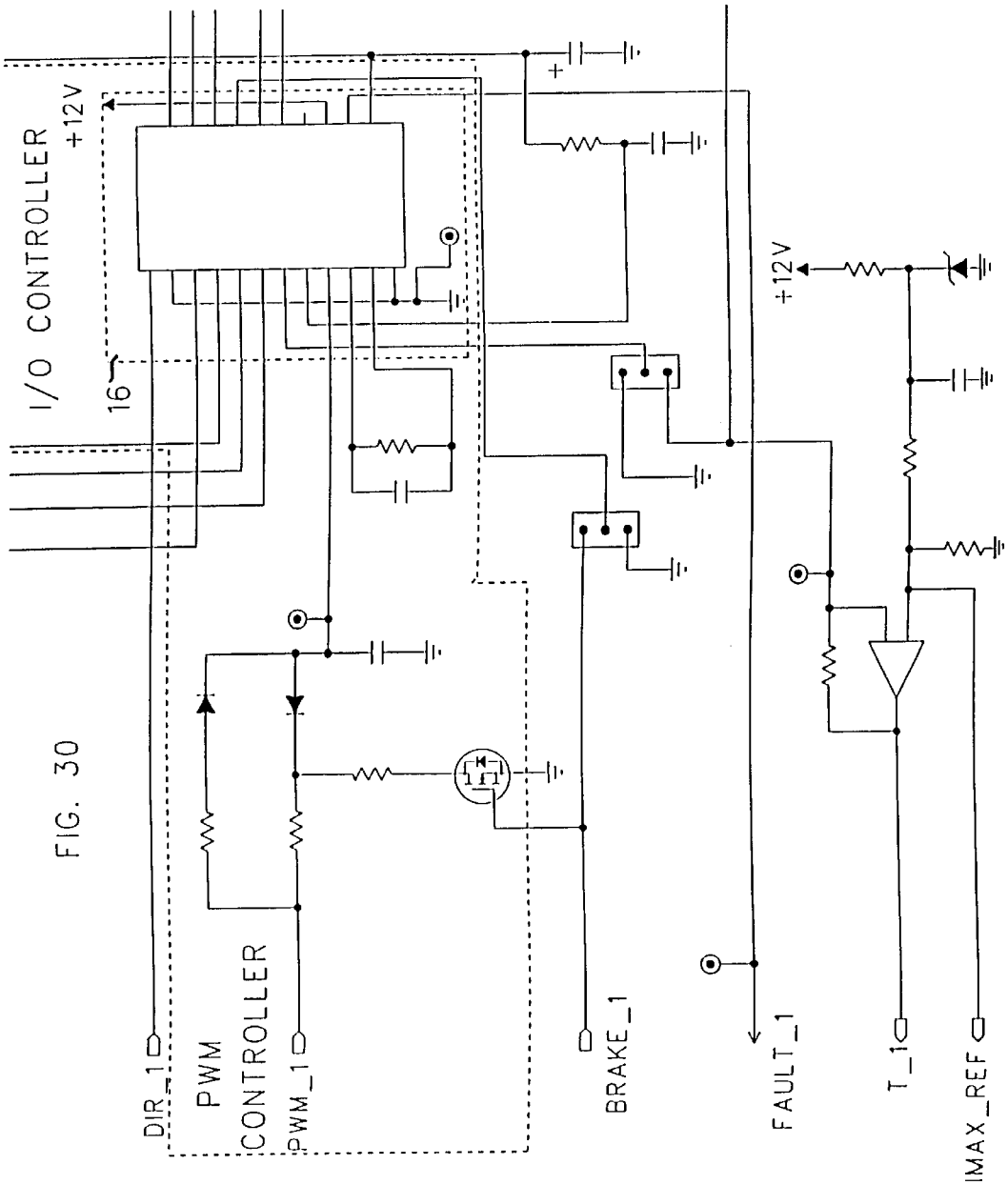
Figure 31:
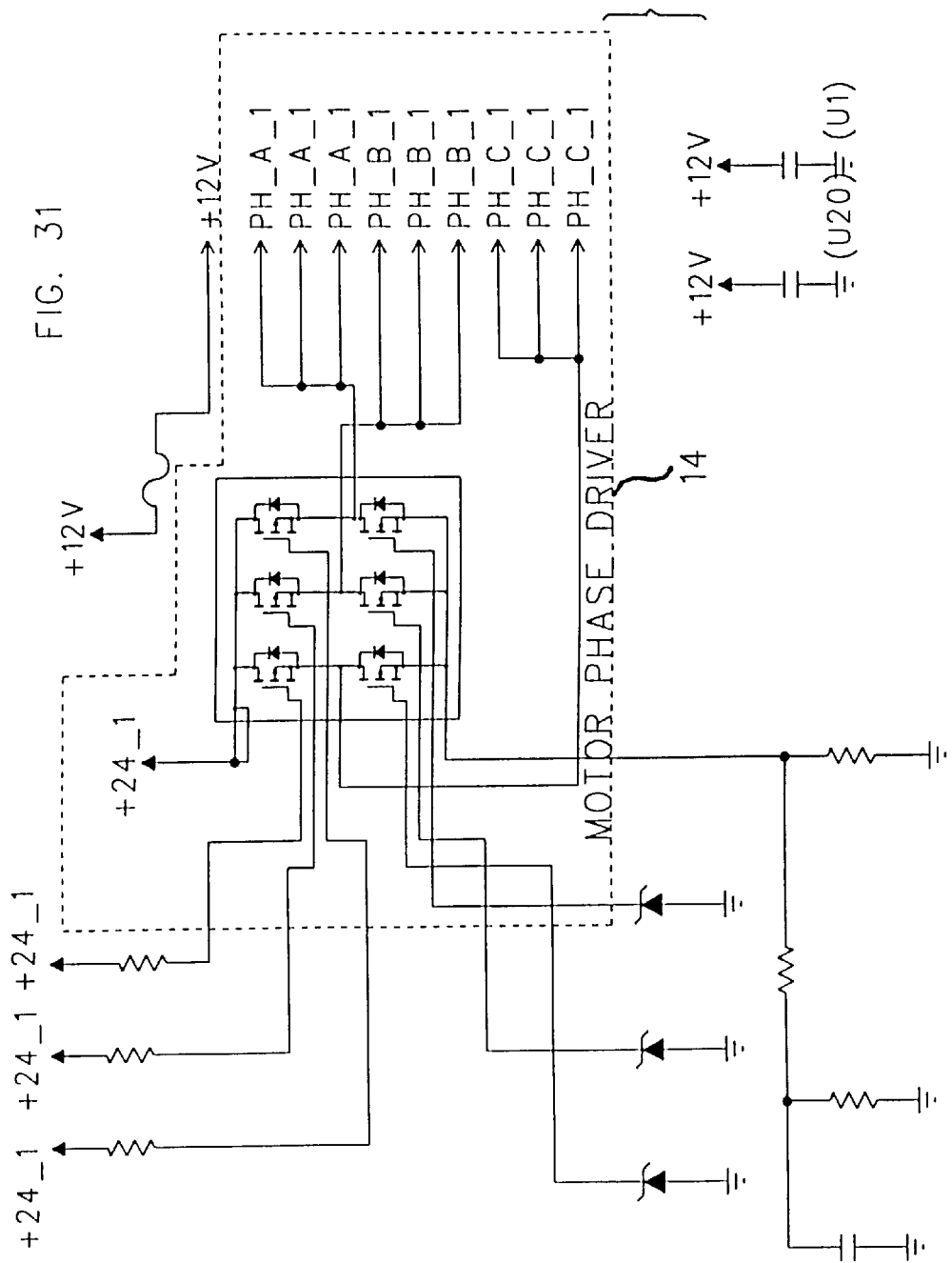
Figure 34:
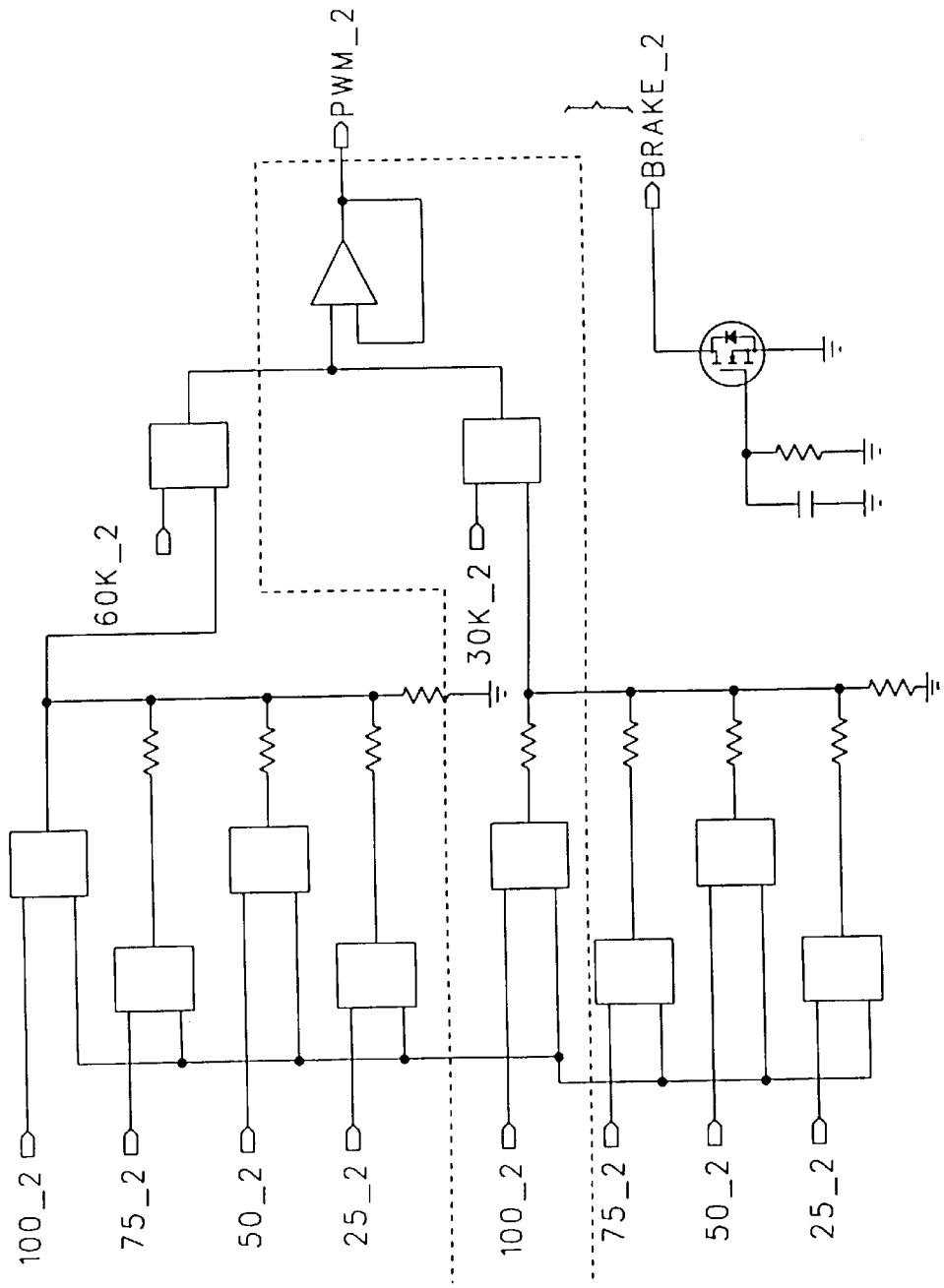
Figure 35:
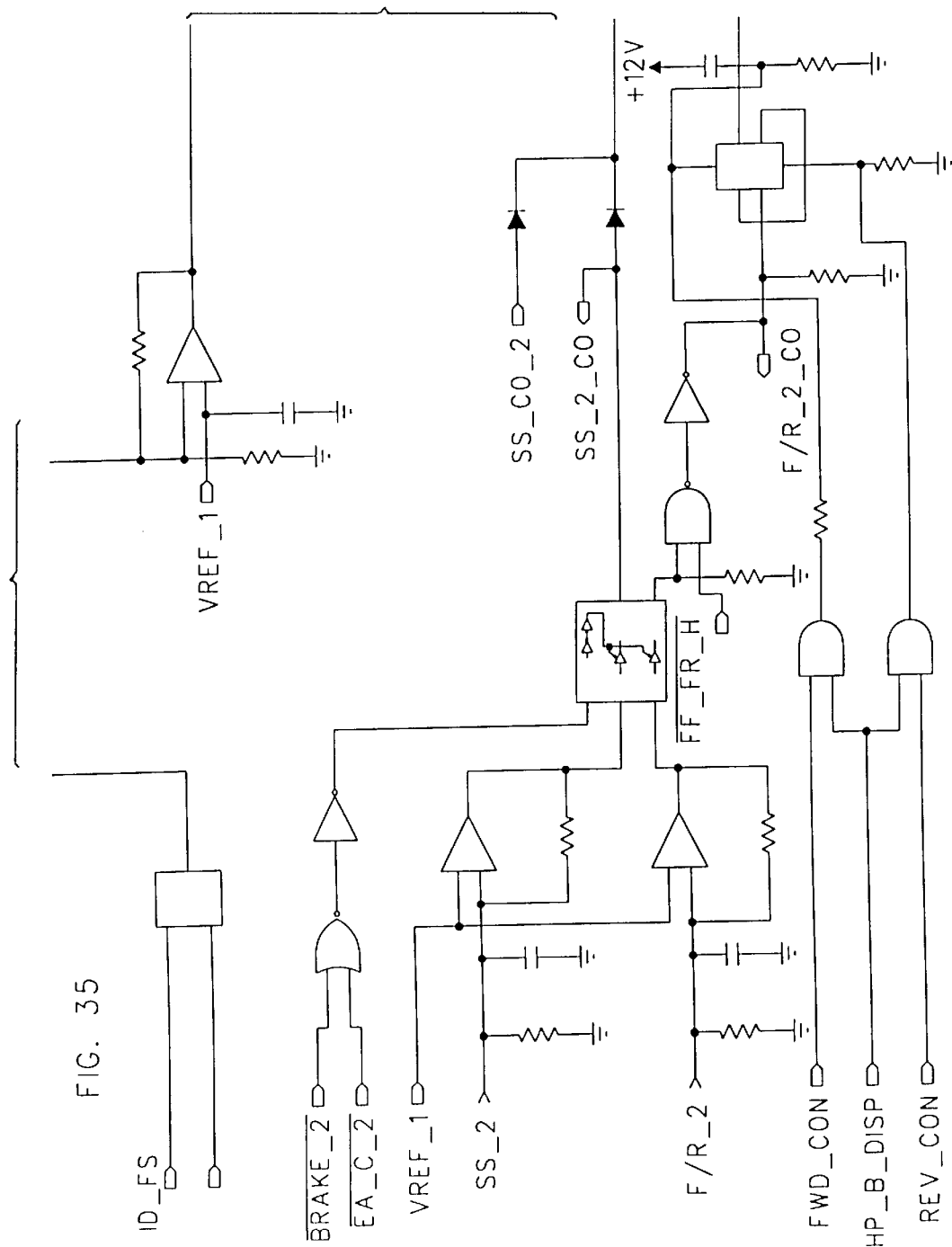
Figure 36:
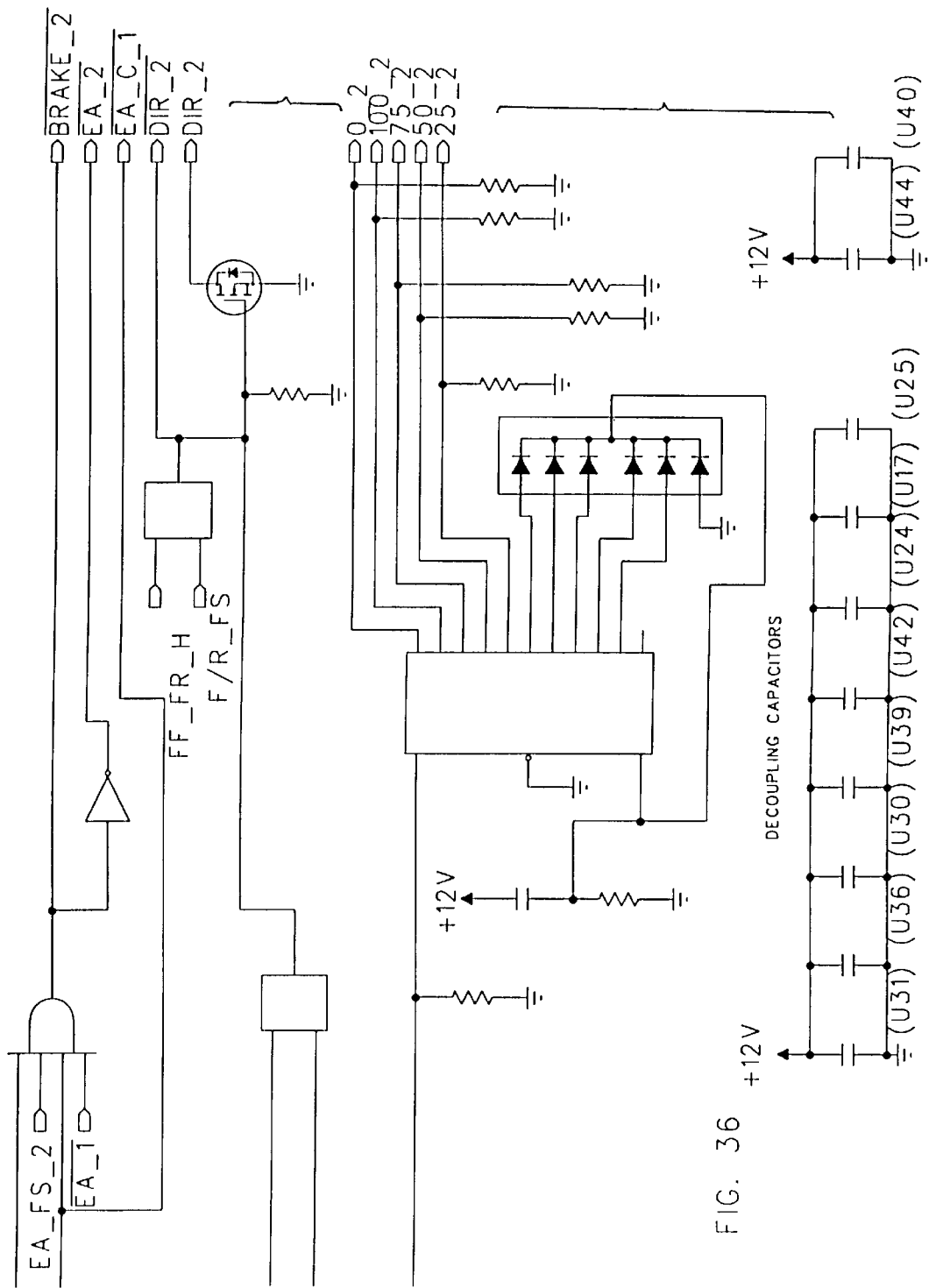

FIGS. 33 through 36 correspond to FIGS. 20 through 23 for channel B. similarly, FIGS. 29 through 31 correspond to FIGS. 25 through 27 for channel B.

Figure 38:
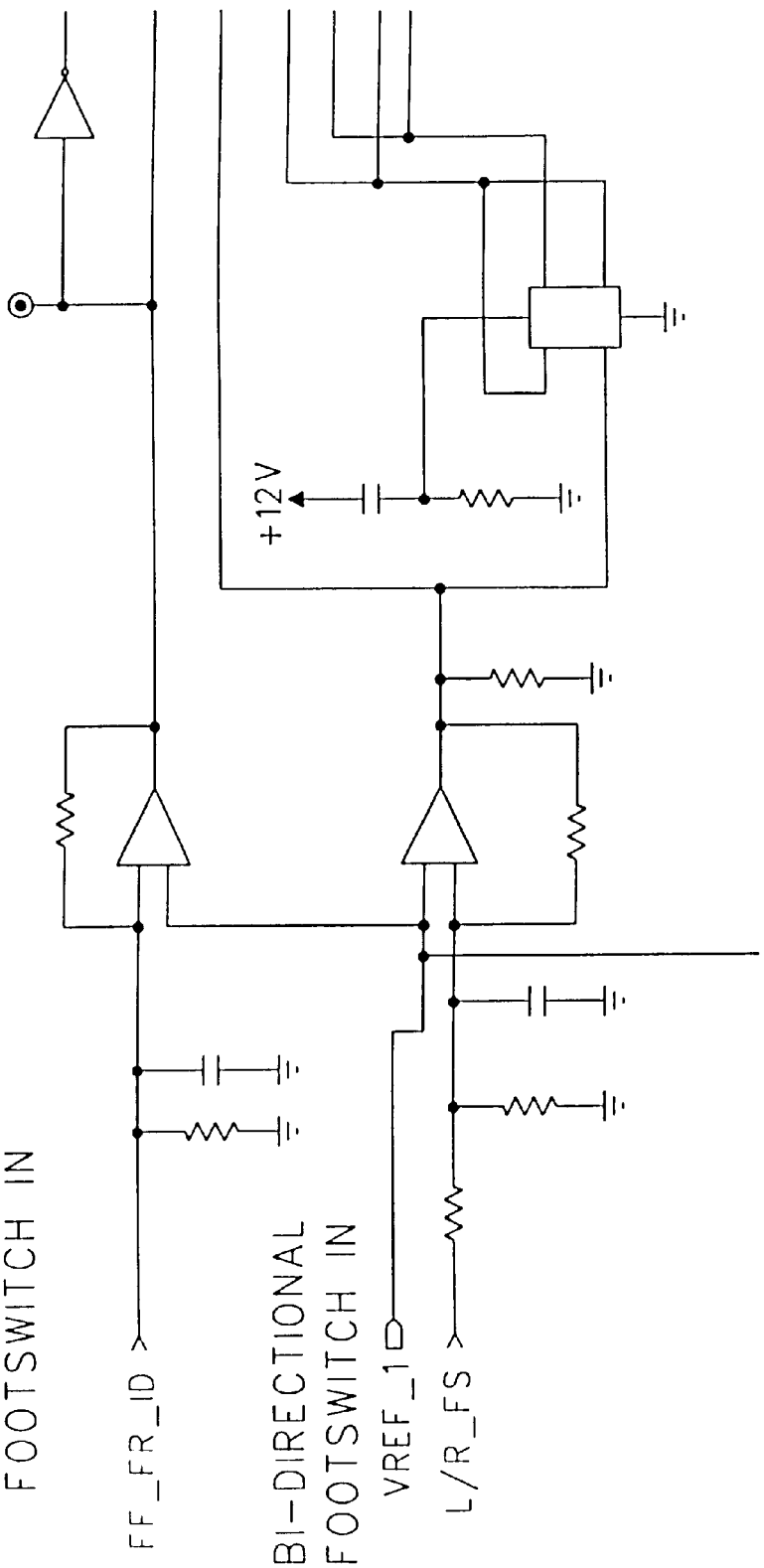
Figure 39:
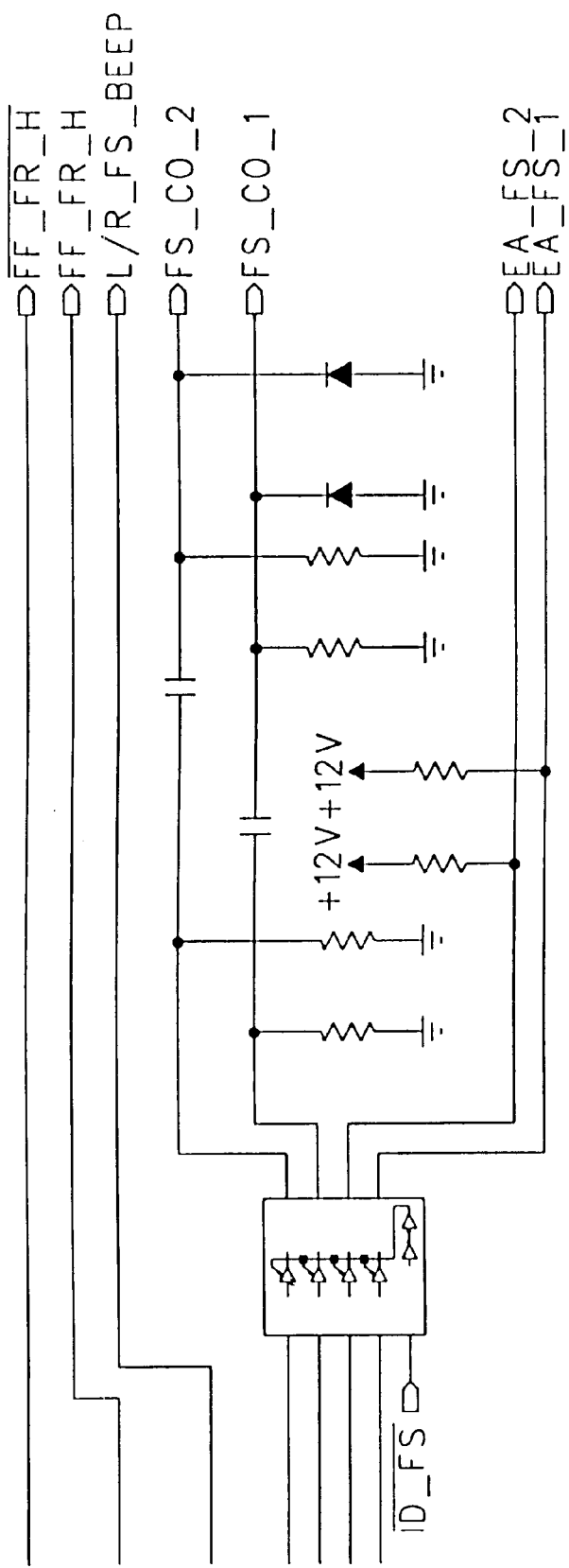
Figure 40:
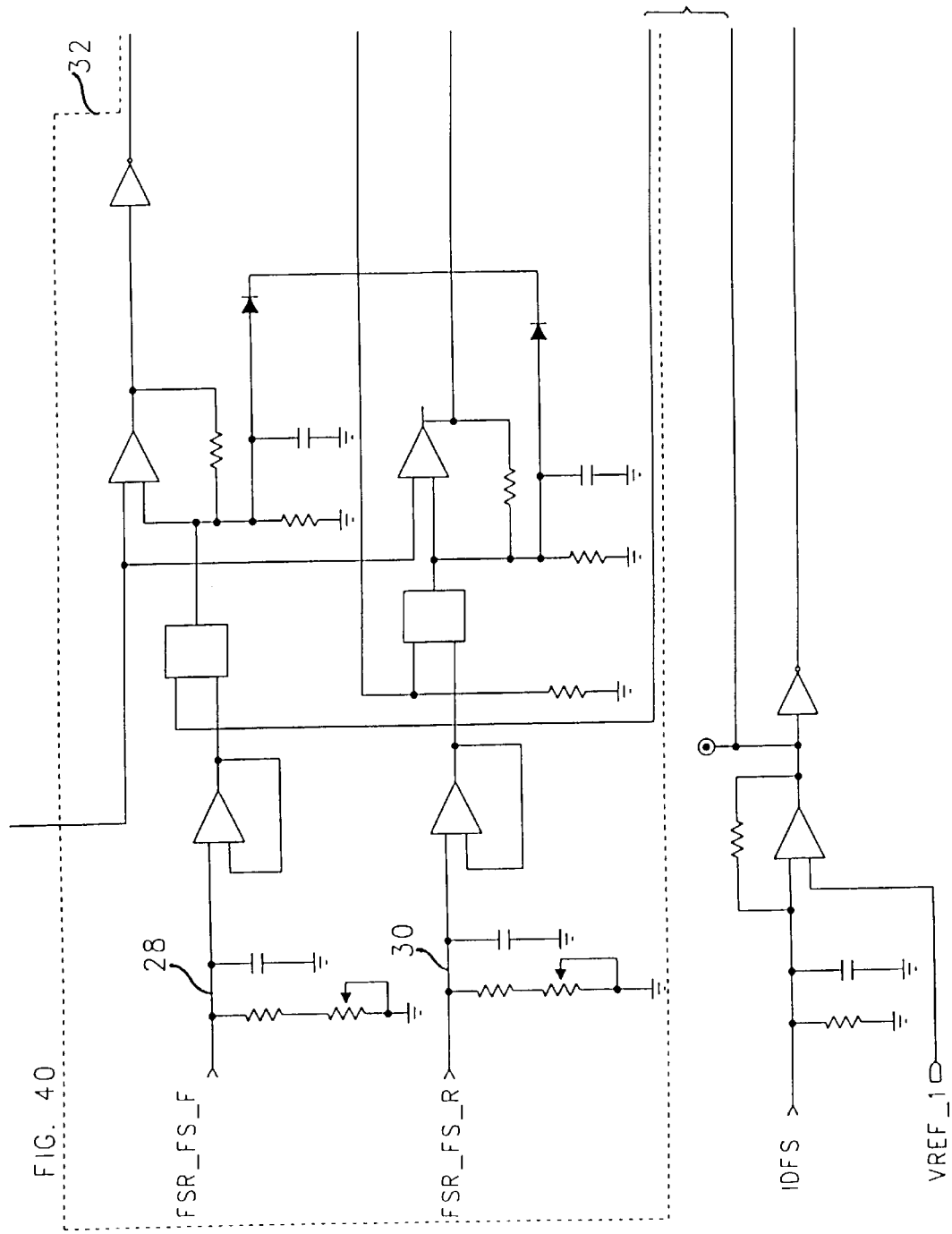
Figure 41:
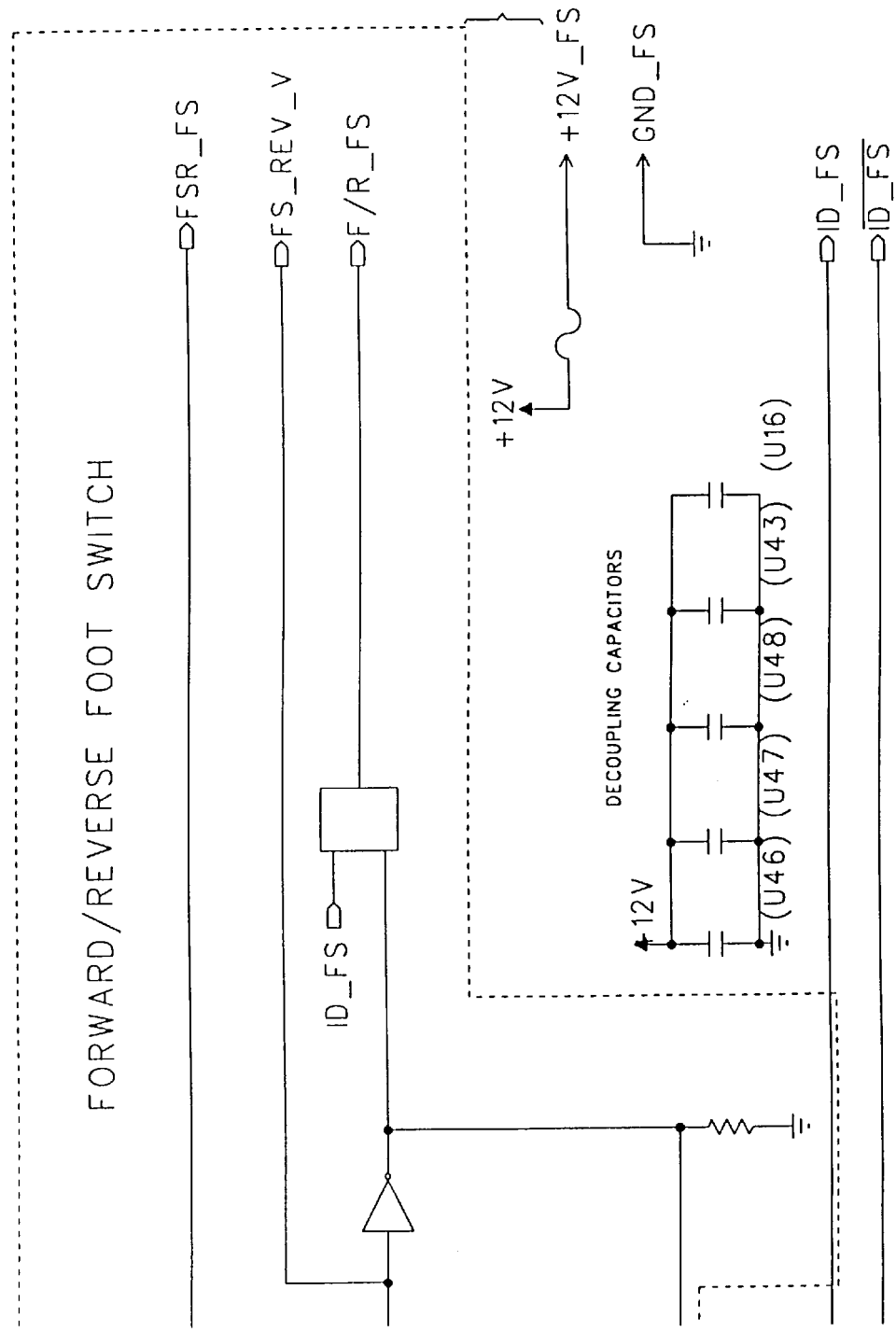
Figure 44:
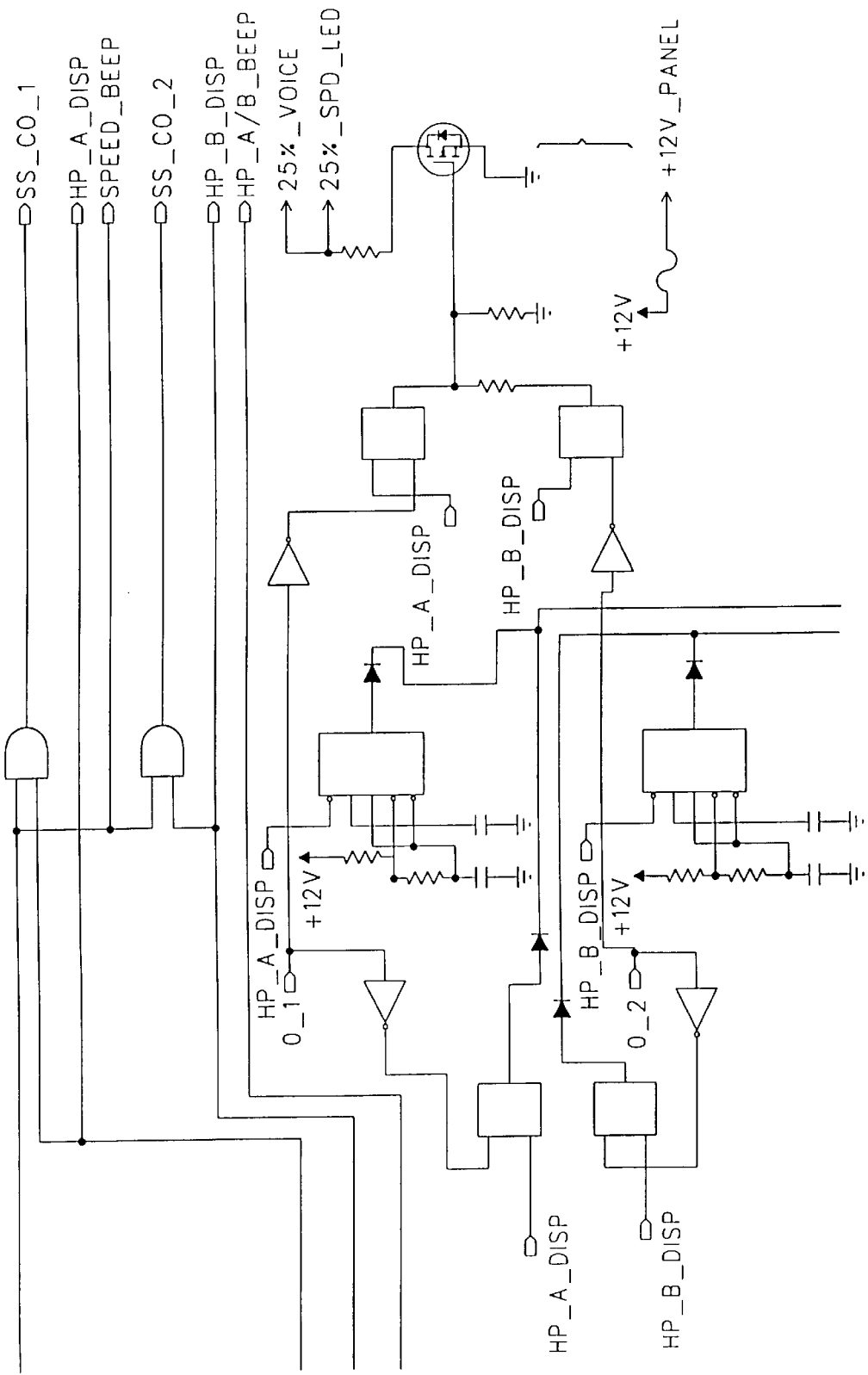

The footswitch circuitry schematic is shown in FIGS. 38 through 41 in which the Uni-directional and bidirectional footswitch control circuitry is shown in FIGS. 38 and 39 and the footswitch speed control circuitry is shown in FIGS. 40 and 41.

Panel Controls

The electrical schematic for the panel controls and of the power control console 70 are shown in FIGS. 43 through 47 and FIGS. 48–51. They include the speed range control from panel switch 26C, the forward and reverse switches F and R for the active channel, all found in schematic drawing 43 and 44.

Figure 45:
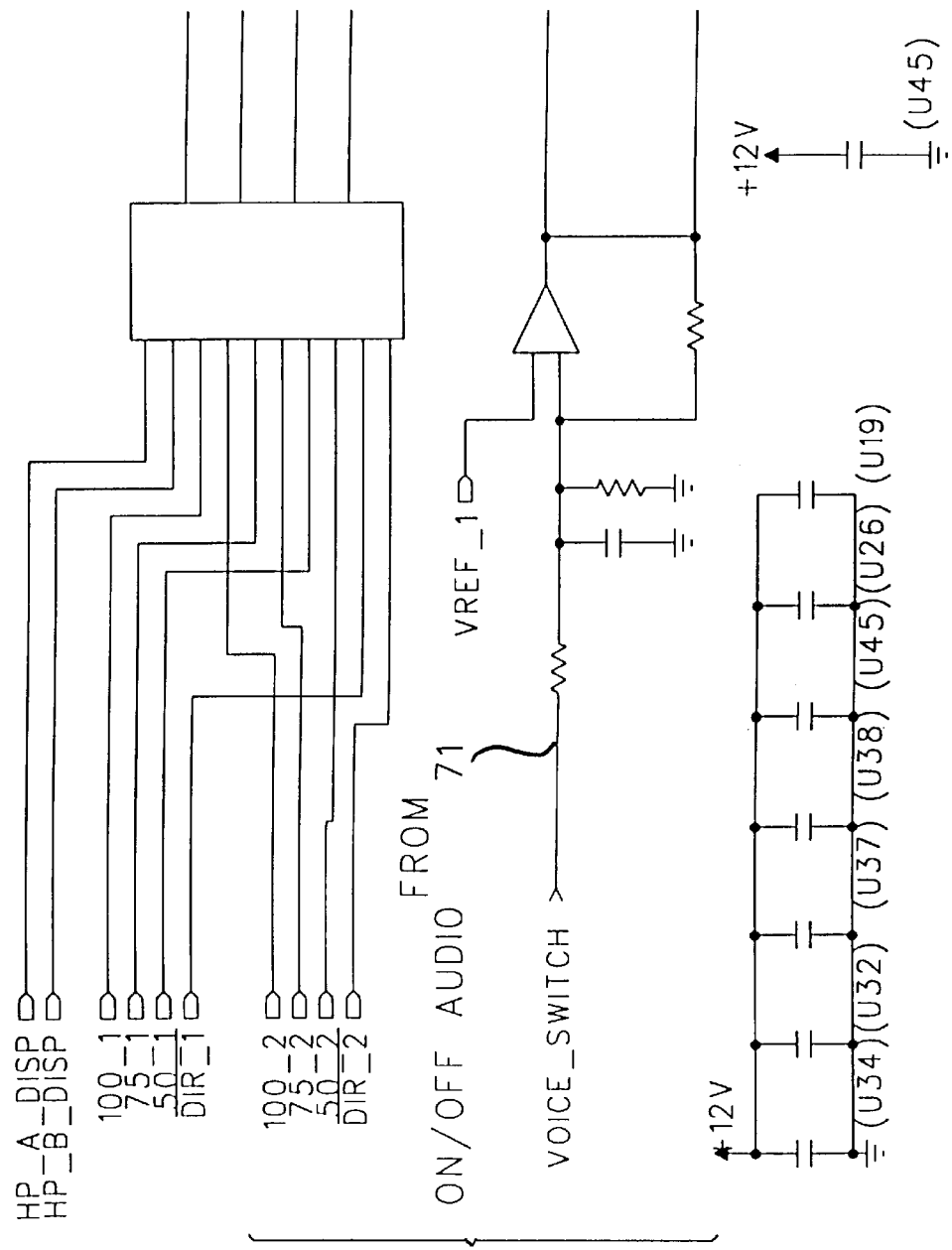
Figure 46:
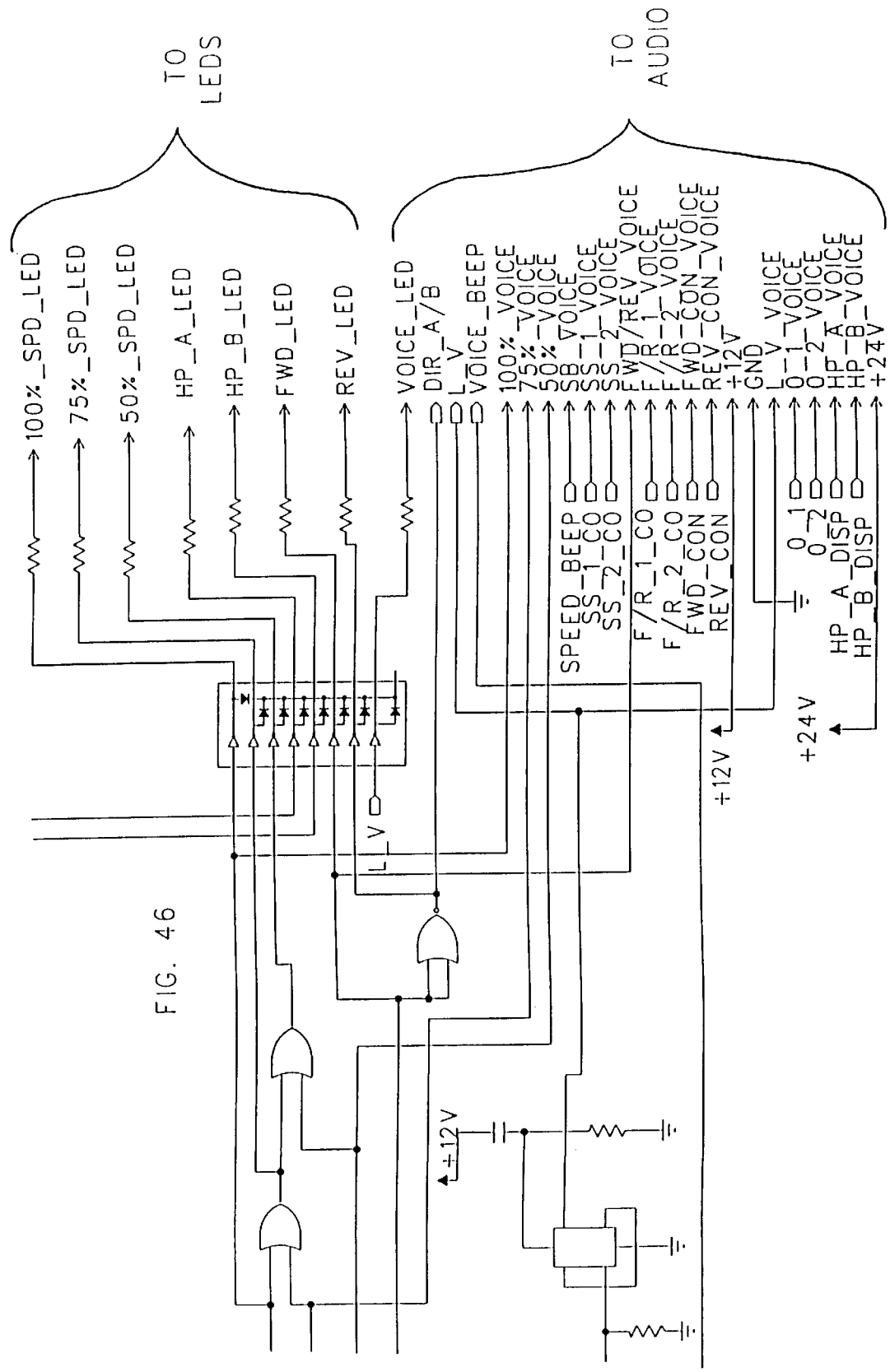
Figure 48:
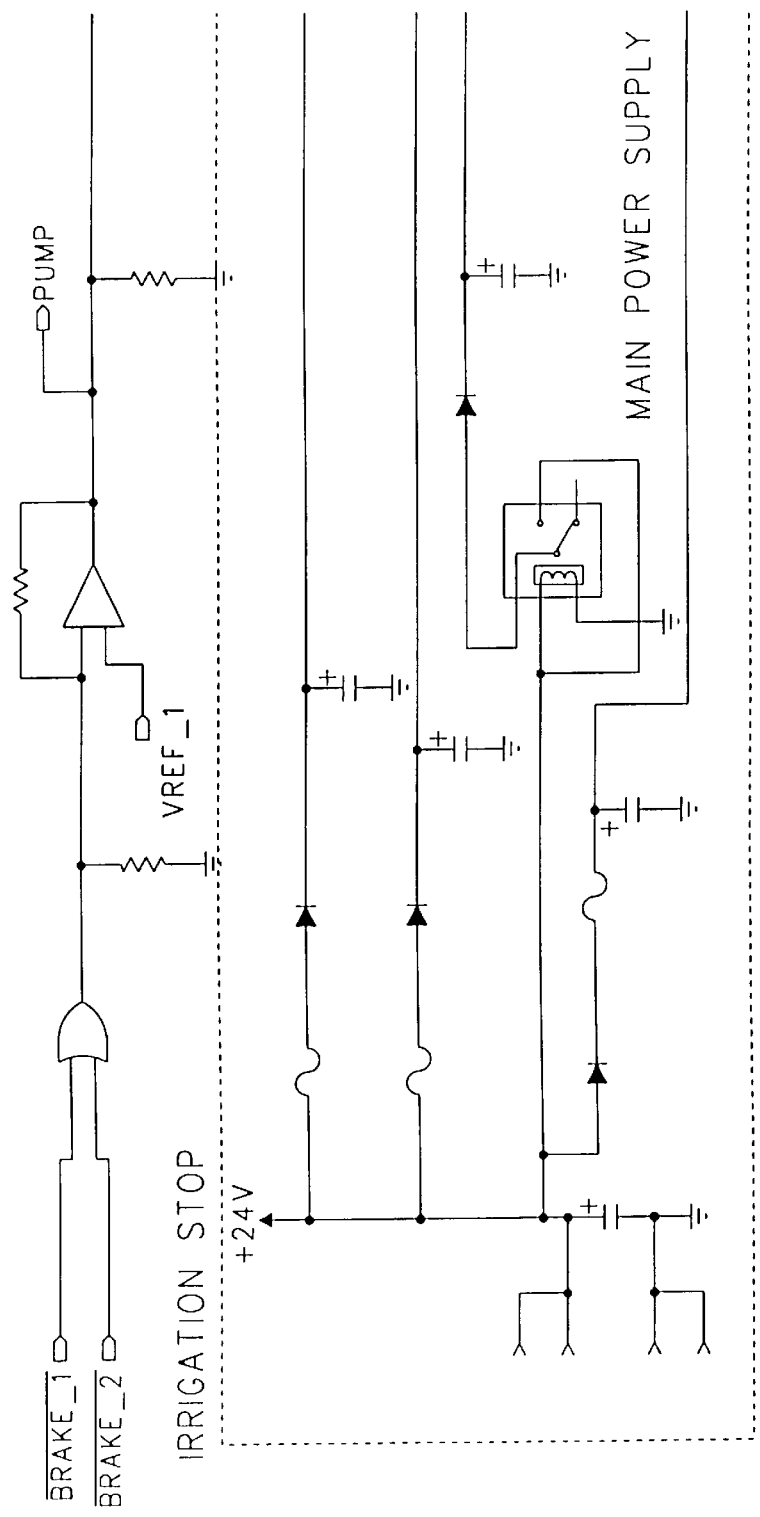
Figure 49:
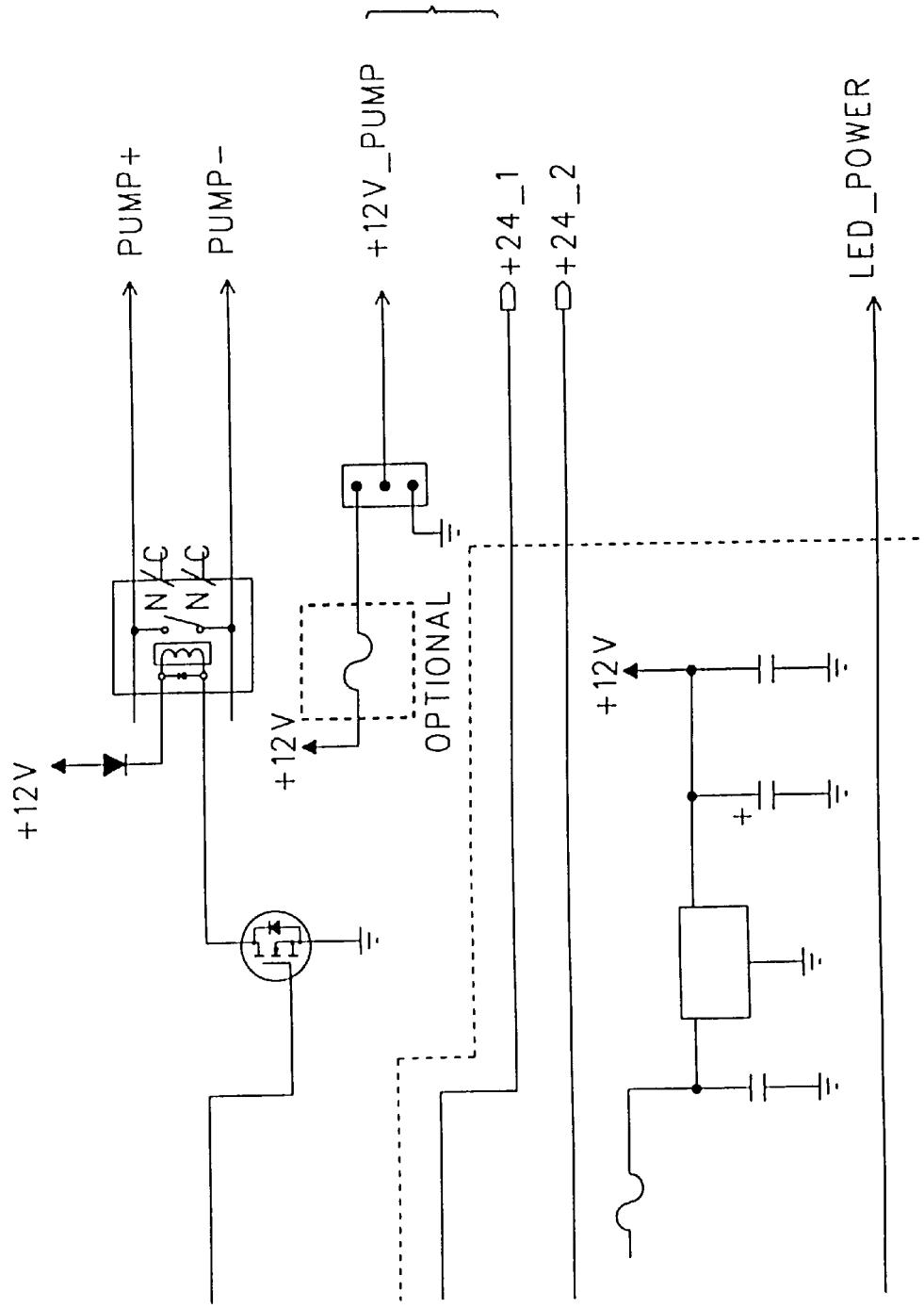
Figure 50:
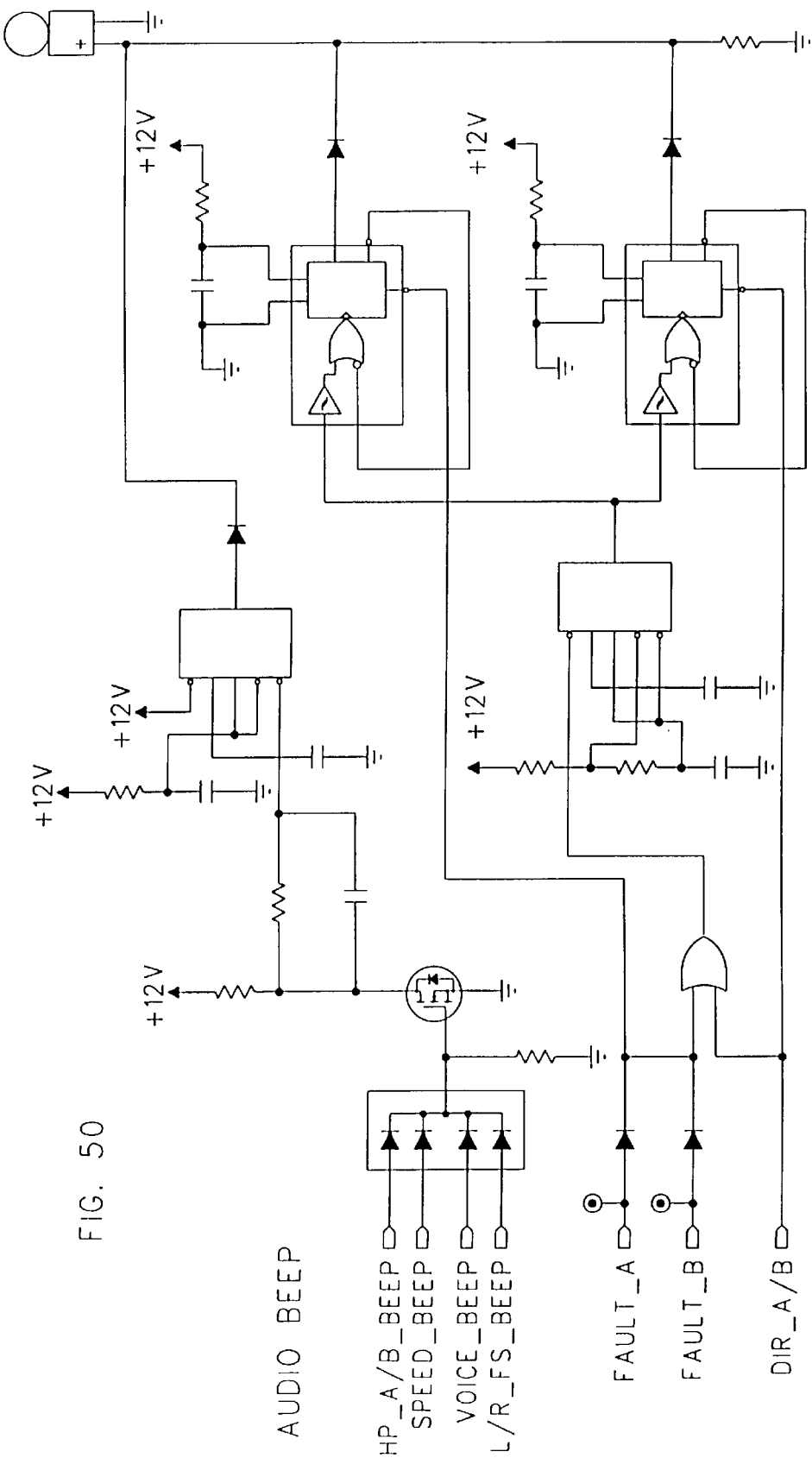
Figure 51:
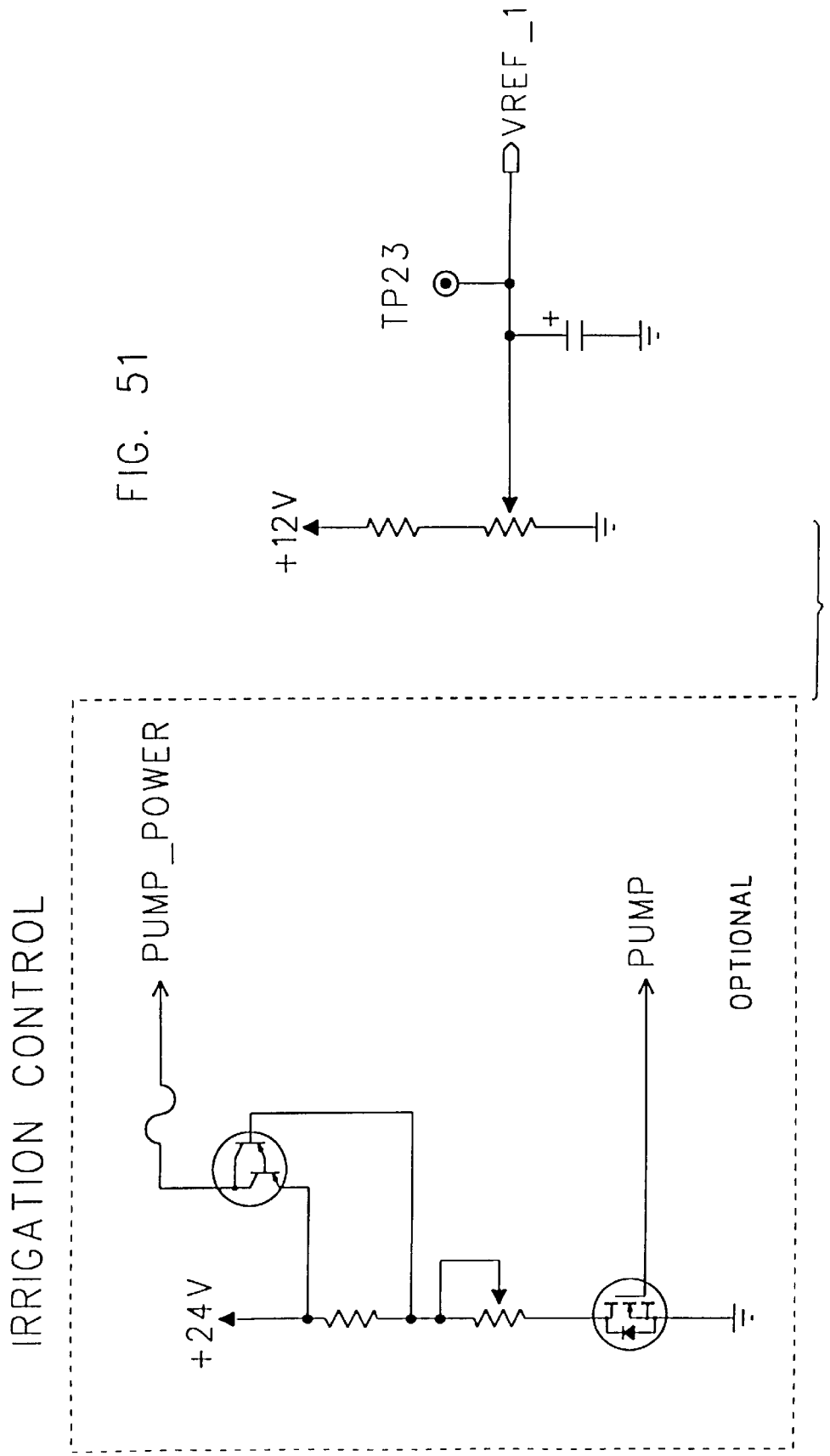

The speed range select input from panel switch 26C and the signal processing to illuminate the speed range LEDs of FIG. 10A is found in FIGS. 45 and 46, upper half. Audio control ON/OFF from audio control switch 71 appears in FIGS. 45 and 46, lower half. MODULES The various modules 12 are available for use with this system may be seen as exemplified by the module 12 of FIGS. 13 and 16-18. For other surgical tools and their modules, reference is hereby made to the co-pending provisional patent applications Ser. No. 60/045,246 and 60/045,250, filed May 1, 1997 and now co-pending non provisional patent applications Ser. No. 09/069,342, filed Apr. 29, 1998 and Ser. No. 09/067,474, filed Apr, 29, 1998, respectively.

Now referring to FIGS. 13–18, a commonly used surgical tool is a bur 17 with its operating head 17H and its special shank 17SS. The special shank has a reduced diameter at its end and no regular drill bit or bur without this precise length step will seat in the collet 12C of module 12. Note that the left or proximal end 12P of the module 12 is square thereby allowing four different directions of mounting in the motor unit 10. Although this feature is not significant for a rotating surgical tool like the bur 17, but other surgical tools such as oscillating saws and Sagittal saws need mounting flexibility. So four different module orientations are available.

Of universal application, however is the feature shown on FIG. 15. The module 12 includes a magnet 12M embedded in the shank of the module. In FIG. 15, this is marked by the dot. The magnet 12M produces a magnetic field in the region of the receptacle for the module and the field is sensed by the Hall effect device 34 which is contained in the housing of the handheld motor unit 11. This sensing of the module 12, which is in place in the motor unit 11, allows automatic control such as speed range selection without the need of selection by the surgeon. It is a backup to his professional tool and speed selection.

The steps of insertion of a burr or other rotating surgical tool, locking as the special shank SS strikes the bottom of its receptacle or chuck and twist locking is illustrated in FIG. 17. The reverse operation in removing the burr 17 or other tool is illustrated in FIG. 18.

The above-described embodiments of the present invention are merely descriptive of its principles and are not to be considered limiting. The scope of the present invention instead shall be determined from the scope of the following claims including their equivalents.

We claim:

1. A surgical power tool comprising
  a control unit including a power source;
  a hand held motor unit connected to said power source including a motor, a housing for said motor, a rotatable shaft driven by said motor and a receptacle on said shaft for receiving a plurality of different tool modules for operation by said motor;
  a plurality of tool modules each of which includes a shank configured to fit in said receptacle, at least some said shanks incorporating a magnet in the shank region thereof; and
  a Hall effect sensor in said housing and responsive to the magnitude of the magnetic field of a magnet of a tool module and further said Hall effect sensor being connected to said control unit for identifying the particular tool module in said receptacle.

2. A surgical power tool as claimed in claim 1 wherein the magnets in said tool modules are selectively variable both as to field strength and polarity; said Hall effect sensor detects such differences in field strength and polarity of said magnets and said control unit is responsive to said detected differences in the magnets to identify the module mounted in said housing and controls the operation of said motor as a function of the magnet strength detected.

3. A surgical power tool as claimed in claim 1 wherein said receptacle is configured to accept said tool modules in a plurality of different radial orientations.

4. A surgical power tool as claimed in claim 1 wherein said housing further includes a cavity;
  a speed control in said cavity including a conductive circuit network connected to said control unit and a layer of semi-conductive material which cooperate to vary electrical resistance with applied physical pressure; and
  a semi-rigid cover plate in sealed relationship with said housing and closing said cavity while overlying said network and semi-conductive material whereby pressure applied to said cover plate varies the amplitude of a motor speed request signal to said control unit and wherein said housing is free of exposed switches and is autoclavable.

5. A surgical power tool comprising
  a control unit including a power source,
  a hand held motor unit including an electric motor and a rotatable shaft driven by said motor,
  a housing enclosing said motor including a cavity,
  a speed control in said housing, said speed control including a resistive network in said cavity connected to said control system;
  a layer of textured semi-conductive material which cooperates with said resistive network to vary electrical resistance with applied physical pressure; and
  a flexible cover plate overlying said network and semi-conductive material whereby pressure on said cover plate varies the electrical resistance of said network and the speed of said motor and wherein said flexible cover plate seals said cavity without any switches exposed and whereby said housing is autoclavable and wherein said rotatable shaft includes a receptacle and said power tool further includes a plurality of tool modules configured to fit in said receptacle, at least some of said tool modules including a magnet, and a single Hall effect sensor in said housing connected to said control unit for identifying which of several of said tool modules is in said receptacle.

6. A surgical power tool as claimed in claim 5 wherein said receptacle is configured to accept said tool modules in a plurality of different radial orientations and wherein said Hall effect sensor identifies different tool modules in said recepticle regardless of the radial orientation of said tool modules.

7. A surgical power tool comprising:
  a power source;
  a hand held motor unit connected to said power source said motor unit including an electrical motor;
  a housing for said motor;
  a rotatable shaft driven by said motor and a receptacle in said shaft;
  a plurality of modules, any one of which may be selectively inserted into said receptacle and a magnet of selected field strength and polarity in certain of said modules inserted in said receptacle; and
  a magnetic field sensor responsive to multiple levels of magnetic field strength;

said magnetic field sensor being positioned in said housing in the region of said receptacle for sensing the presence and, magnetic field strength of a magnet and thereby identifying the particular module in said receptacle;

said sensor connected to said power source to control said electrical motor.

8. A surgical power tool as claimed in claim 7 wherein said receptacle is configured to accept said modules in a plurality of different radial orientations.

9. A surgical power tool comprising:

a control unit including a power source;

a hand held motor unit connected to said power source including a housing including a cavity and an electrically driven motor in said housing;

a rotatable shaft driven by said motor, said shaft including a receptacle;

a plurality of tool modules, any one or which may be selectively inserted into said receptacle, a magnet in at least some of said modules, said magnets being of varying strengths in different modules;

a Hall effect sensor in said housing connected to said control unit and positioned to sense the magnetic strength of a magnet in said receptacle for identifying the particular module in the receptacle;

a speed control in said housing, said speed control including a conductive circuit network in said cavity connected to said control system and a layer of textured semi-conductive material in said cavity which cooperates with said semi-conductive material to vary resistance with applied physical pressure; and a cover plate overlying said network and semi-conductive material in cavity sealed relationship with said housing;

said cover plate and housing being impervious to moisture and said speed control and motor being unaffected by autoclave temperatures whereby said entire power tool may be autoclaved.

10. A handheld motor unit for driving powered surgical instruments comprising:

a motor;

a shaft driven by said motor;

a receptacle on said shaft for receiving a variety of surgical tool modules to be driven by said motor;

a housing for said motor;

said housing being sealed with said shaft, receptacle and a source of power extending outside of said sealed housing;

said housing having a proximal end and a distal end and including a flexible wall portion;

said flexible wall portion having a pattern thereon tapering in size along the length thereof;

variable electrical resistance means within said housing in the region of said flexible wall portion and connected to said source of power;

said variable electrical resistance means being responsive to variable deflection of said flexible wall portion corresponding to the taper of the pattern on the surface of said flexible wall portion to similarly vary the speed of said motor and;

a surgical tool in said receptacle.

11. A handheld motor unit in accordance with claim 10 wherein said receptacle includes a Hall effect device which responds to the magnetic field strength of magnetic means in the region of said receptacle as a means of identifying the surgical tool in said receptacle.

12. A handheld motor unit in accordance with claim 11 wherein said Hall effect device is connected to the source of power for said motor to control the operation of the motor as a function of the detection of magnetic means in the region of said receptacle.

13. A handheld motor unit in accordance with claim 11 wherein said Hall effect device is positioned in said housing adjacent to said receptacle.

14. A handheld motor unit in accordance with claim 11 wherein said receptacle is configured to receive a surgical tool in a plurality of orientations and said Hall effect device is positioned in said housing to respond to the presence of magnetic means regardless of the surgical tool orientation selected.

15. A handheld motor unit in accordance with claim 10 wherein said motor unit is autoclavable.

16. A handheld motor unit in accordance with claim 10 wherein said variable resistance means includes a plurality of sections, each of said sections responsive to flexible housing wall deflection to produce a different signal for control of said motor unit said flexible wall portion having discrete patterns thereon corresponding to the location of individual ones of said plurality of sections of said variable resistance means.

17. A handheld motor unit in accordance with claim 10 wherein said housing is elongated and said flexible wall portion is elongated and extends along said housing;

said variable resistance means being located in a spaced array along said elongated flexible wall portion to provide a linear array of controls for said motor.

18. A handheld motor unit in accordance with claim 16 wherein said housing includes a proximal end adjacent to said motor and a tapered distal portion adjacent to said receptacle; and wherein said variable resistance means extends into the tapered portion of said housing and exhibits a variable resistance characteristic which varies as a function of the position along the taper of said housing.

19. A handheld motor unit in accordance with claim 16 wherein said housing includes a substantially straight portion and said flexible wall portion extends along at least part of said straight portion; and pressure sensitive conductive means located beneath said flexible wall portion in the substantially straight portion of said housing to respond to finger pressure applied to deflect said flexible wall and respond to such finger pressure to constitute a switch operation.

20. A handheld motor unit in accordance with claim 16 including a plurality of pressure sensitive conductive means within said housing, each of said pressure sensitive conductive means responsive to finger pressure at a different location on said flexible wall portion in the substantially straight portion of said housing to provide a plurality of different switch operations.

21. A powered surgical tool drive system comprising:

a control unit including a power source;

a handheld motor unit including a motor and a rotatable drive shaft driven by said motor;

a receptacle on said drive shaft for holding any one of a plurality of surgical tools;

a housing for said handheld motor unit sealing said motor unit within said housing except for an outwardly extending driving portion of said shaft and said receptacle and power supply for said motor from said control unit;

said housing having a flexible wall portion;

finger pressure operated motor controls for said motor within said housing positioned beneath said flexible wall portion to be operated by flexing said flexible wall portion with finger pressure while holding said handheld unit;

a Hall effect device within said housing and positioned in the region of said receptacle for surgical tools;

a series of surgical tools including portions dimensioned for mounting in said receptacle and for rotation by said shaft;

at least some of said surgical tools each including magnetic means of different magnetic field strength in the portion of the surgical tool positioned in the region of said Hall effect device while in said receptacle; and means in said system responsive to the detection of the field strength of said magnetic means by said Hall effect device for controlling the operation of the motor consistent with the operating characteristics of such surgical tool.

22. A powered surgical tool drive system in accordance with claim 20 wherein said motor controlling means responding to said Hall effect device is located in said control unit.

23. A powered surgical tool drive system in accordance with claim 21 wherein said motor controlling means responding to said Hall effect device serves to limit the operating speed of said motor to a speed range compatible with the tool detected.

24. A powered surgical tool drive system in accordance with claim 19 wherein said finger pressure operated motor controls within said housing include a pressure variable resistance membrane below the flexible wall portion of said housing, said pressure variable resistance membrane coupled to said motor unit to control the speed thereof as a function of finger pressure applied to said flexible wall portion of said housing.

25. A powered surgical tool drive system in accordance with claim 22 wherein said pressure sensitive conductive means is electrically coupled to said control unit; and said control unit being operative to limit the speed of said motor as commanded by finger pressure on said flexible wall portion of said housing as indicated by a signal from said Hall effect device.

26. A powered surgical tool drive system in accordance with claim 19 wherein said finger pressure operated motor controls in said housing include at least one pressure sensitive resistance means responsive to finger pressure on a discrete area of said flexible wall portion of said housing to provide a switching operation for said motor.

27. A power operated surgical tool drive system in accordance with claim 19 wherein said control unit includes switch means duplicating at least certain of said finger pressure operated motor controls of said handheld motor unit.

28. A power operated surgical tool drive system in accordance with claim 19 wherein said control unit includes at least two input connections for simultaneously powering and controlling at least two handheld motor units independent of each other.

29. In a surgical power tool including a power source, a handheld motor unit connected to said power source and including a receptacle for receiving a variety of surgical tools to be operated by said handheld motor unit;

the improvement wherein said handheld unit includes radiation detection means in the region of said receptacle;

said radiation detection means being capable of distinguishing radiation of a plurality of different levels and a variety of surgical tool modules include a proximal end configured to be received by said receptacle, certain of said surgical tool modules include a radiation source of different radiation levels therein detectable by said radiation detector;

said radiation source coupled to said power source to control the operation of said motor unit consistent with the operating standards of the surgical tool module presently in the receptacle.

30. In a surgical power tool in accordance with claim 29 wherein said handheld motor unit includes manual controls for operating the surgical tool module, the operation of the motor unit as controlled by said radiation source overriding the manual control of the surgical tool.

31. In a surgical power control in accordance with claim 29, a surgical tool module including a shaft having a distal end and a proximal end adapted to be received by a powered unit;

a surgical tool at the distal end of said shaft; and a radiation source secured to said surgical tool providing identification of the particular surgical tool module.

32. A surgical tool module comprising a shaft including a distal end and a proximal end;

a surgical tool secured to said distal end;

the proximal end of said surgical tool module adapted to be received by and operated by a power source;

said surgical tool module including a radiation source of a selected one of a plurality of radiation strengths for identification thereof by a multiple strength radiation detector.

33. A surgical tool module in accordance with claim 32 wherein said radiation source comprises a magnet of selected field strength.

34. A surgical tool in accordance with claim 33 wherein said magnet is embedded in said shaft in a preselected polarity position.

35. A handheld control unit for powered instruments in accordance with claim 24 wherein said pressure sensitive conductive means comprises:

a layer of textured semi-conductive material which cooperates with said resistive network to vary electrical resistance with applied physical pressure; and said flexible wall portion comprising a flexible cover plate overlying said network and semiconductive material whereby pressure on said cover plate varies the electrical resistance of said network and the operation of a powered instrument in said receptacle, said pressure sensitive variable resistance comprising;

a layer of textured semi-conductive material which cooperates with said resistive network to vary electrical resistance with applied physical pressure; and said flexible wall portion comprising a flexible cover plate overlying said network and semi-conductive material whereby pressure on said cover plate varies the electrical resistance of said network and the operation of a powered instrument in said receptacle.

36. A handheld control unit for powered instruments in accordance with claim 35 including:

a speed control in said housing, said speed control including a conductive circuit network in said cavity connected to said control system and a layer of textured semi-conductive material in said cavity which cooperates with said semi-conductive material to vary resistance with applied physical pressure; and a cover plate forming the flexible portion of said housing overlying said network and semi-conductive material.

37. A handheld motor unit for instruments in accordance with claim 35 wherein said handheld control unit is autoclavable.

38. A handheld control unit for powered instruments in accordance with claim 35 wherein said variable resistance means includes a plurality of sections, each of said sections responsive to flexible housing wall deflection to produce a different signal for control of an instrument in said receptacle.

39. A handheld unit for powered instruments in accordance with claim 35 wherein said housing is elongated and said flexible wall portion is elongated and extends along said housing; said variable resistance means being located in a spaced array along said elongated flexible wall portion to provide a linear array of controls for an instrument in said receptacle.

40. A handheld control unit for powered instruments in accordance with claim 35 wherein said housing is elongated with distal end enclosing a shaft and receptacle for receiving an instrument to be powered and a proximal end for connection to a power supply for the instrument;

the distal end of said housing being tapered and wherein said flexible wall portion extends into said tapered portion of said housing.

* * * * *